(12) United States Patent
Harding et al.

(10) Patent No.: US 8,404,251 B2
(45) Date of Patent: Mar. 26, 2013

(54) LPRG AS A CHAPERONE OF IMMUNE ADJUVANTS

(75) Inventors: Clifford V. Harding, Shaker Heights, OH (US); W. Henry Boom, Shaker Hts, OH (US); Michael G. Drage, Cleveland Heights, OH (US); Nicole D. Pecora, Cleveland Heights, OH (US)

(73) Assignee: Case Western Reserve University, Cleveland, OH (US)

( * ) Notice: Subject to any disclaimer, the term of this patent is extended or adjusted under 35 U.S.C. 154(b) by 383 days.

(21) Appl. No.: 12/693,896

(22) Filed: Jan. 26, 2010

(65) Prior Publication Data

US 2011/0033484 A1    Feb. 10, 2011

Related U.S. Application Data

(60) Provisional application No. 61/147,304, filed on Jan. 26, 2009.

(51) Int. Cl.
*A61K 39/04* (2006.01)

(52) U.S. Cl. .................. 424/248.1; 424/278.1; 530/350; 530/351

(58) Field of Classification Search ........................ None
See application file for complete search history.

(56) References Cited

PUBLICATIONS

Pecora, Nicole (Dissertation Ph.D.Year: 2008 Corporate Source/Institution: Case Western Reserve University. pp. 1-181).*

* cited by examiner

*Primary Examiner* — Jennifer Graser
(74) *Attorney, Agent, or Firm* — Tarolli, Sundheim, Covell & Tummino LLP

(57) ABSTRACT

An adjuvant combination that stimulates immune activation or response includes a hydrophobic immune adjuvant and a pathogen derived lipoprotein that chaperones the hydrophobic immune adjuvant to an immune receptor.

2 Claims, 16 Drawing Sheets

B

```
  1 mrtprrhcrriaviavlaavsiaatvvagcss----------gskpsggplpd
  1 mkhp--pcsvvaaatailavvlaiggcstegdagkasdtaatasng---d
        ⟨──α1──⟩      ⟨─β1─⟩    ⟨─β2─⟩      ⟨β3⟩
 41 akplveeataqtkalksahmvltvngkipclslktlsgdittnp-taatg
 46 aamllkqatdamrkvtcmhvrlavtgdvprlrvtklegdisntpqtvatg
     ⟨─β3─⟩ ⟨─β4─⟩  ⟨β5⟩   ⟨β6⟩ ⟨α2⟩
 90 nvkltlggsdidadfvvfdgilyatl-tprqwsdfgpaadiycpaqvlnp
 96 satllvgnksedakfvyvdghlysdlgqpctytdfgngasiynvsvlldp
        ⟨α3⟩   ⟨─β7─⟩  ⟨─β8─⟩  ⟨α4⟩ ⟨α5⟩
139 dtglanvlanfadakaegrdtingqntirisgkvsaqavnqiappfnatq
146 nkglanllanlkdasvagsqqadgvattkitgnssaddiatlagsrltse
         ⟨─β9─⟩    ⟨─β10─⟩  ⟨β11⟩
189 pv---patvwiqetgdrqlaqaqldrgsgrsvqmtlskwgekvqvtkppv
196 dvktvpttvwiasdgsshlvqiqiaptkdtsvtltmsdwgkqvtatkpv- 236 s
    -
```

Fig. 1B

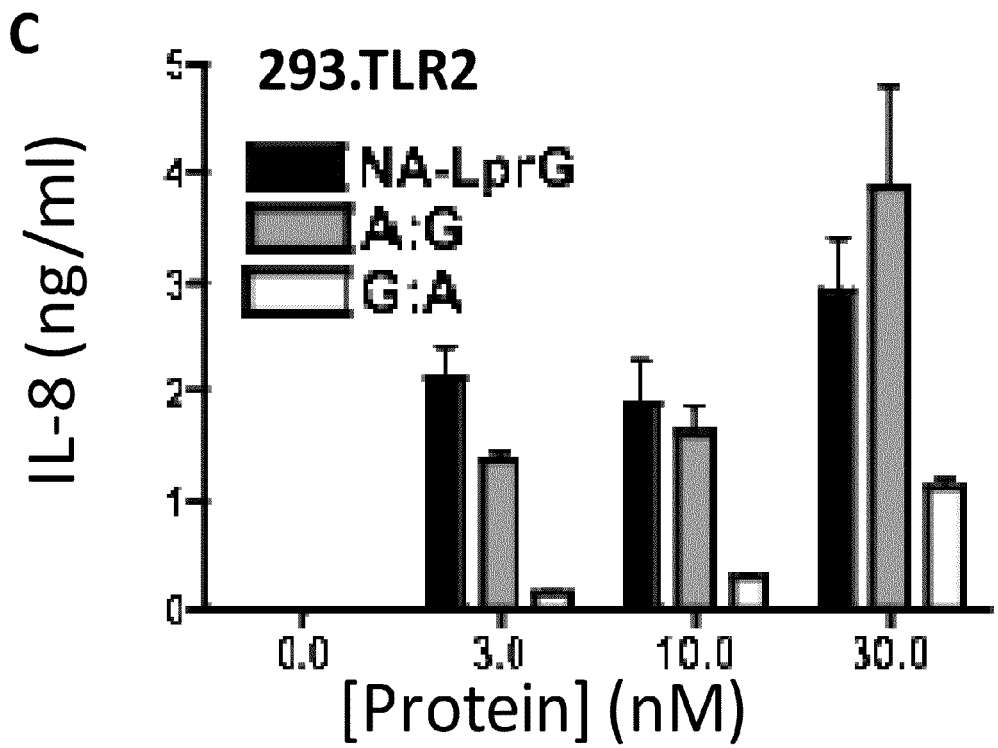
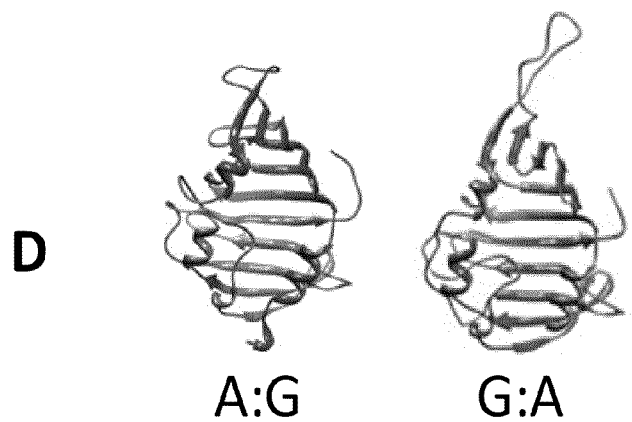
| NTD | CTD | activity |
|---|---|---|
| A | A | - |
| G | G | ++ |
| A | G | +++ |
| G | A | + |
Fig. 1C-D

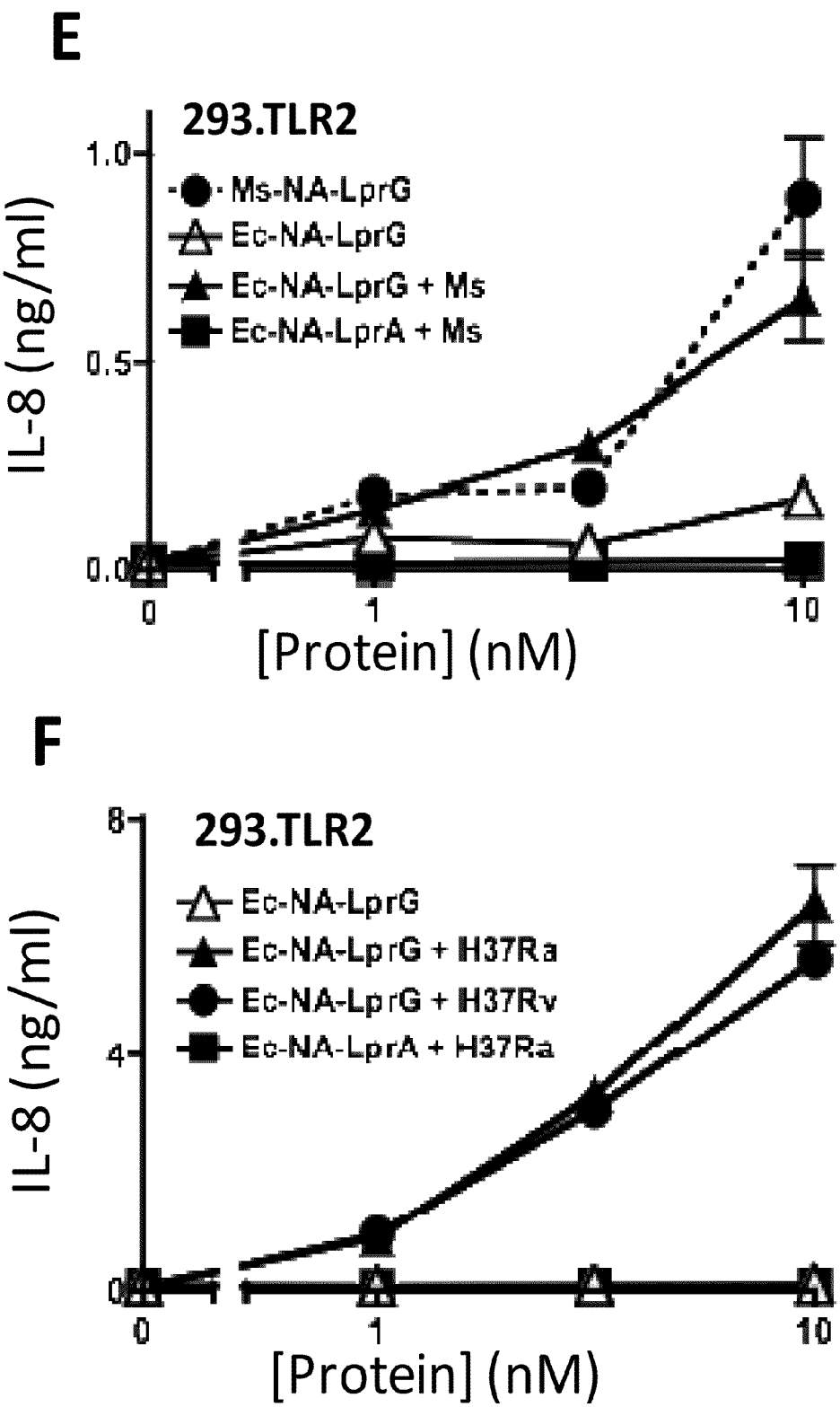
Fig. 1E-F

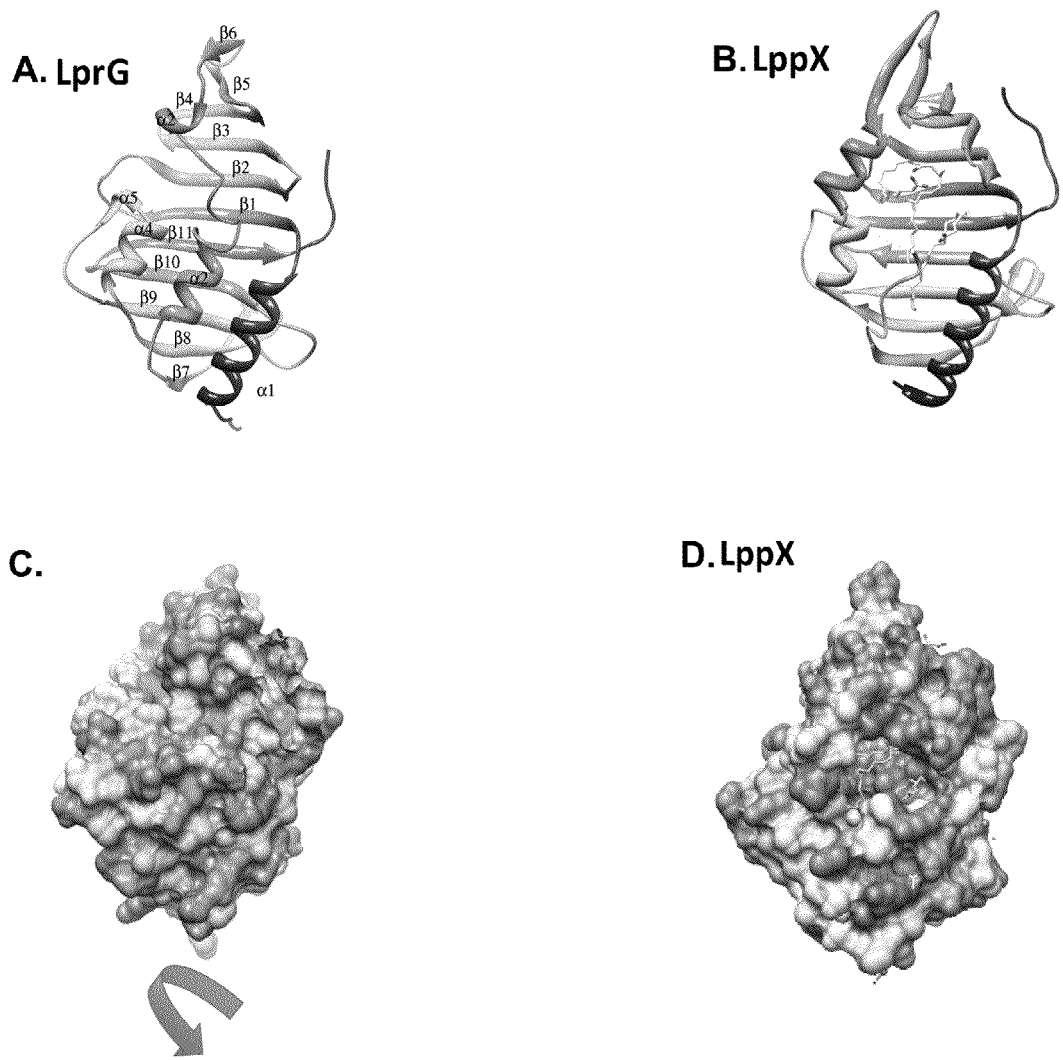
Fig. 2A-D

E. LprG  F. LprG pocket  G. LprG slab
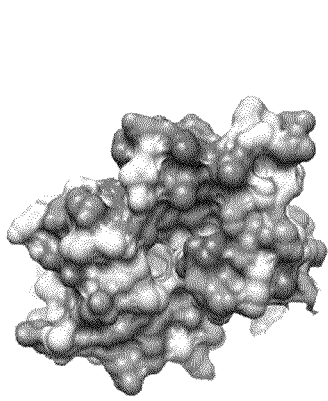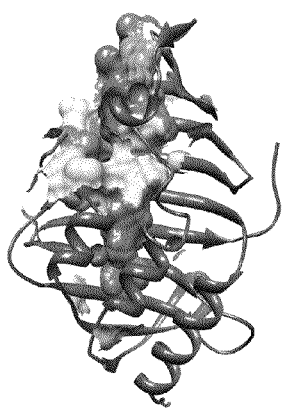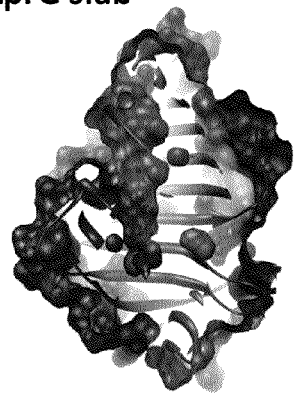
Fig. 2E-G

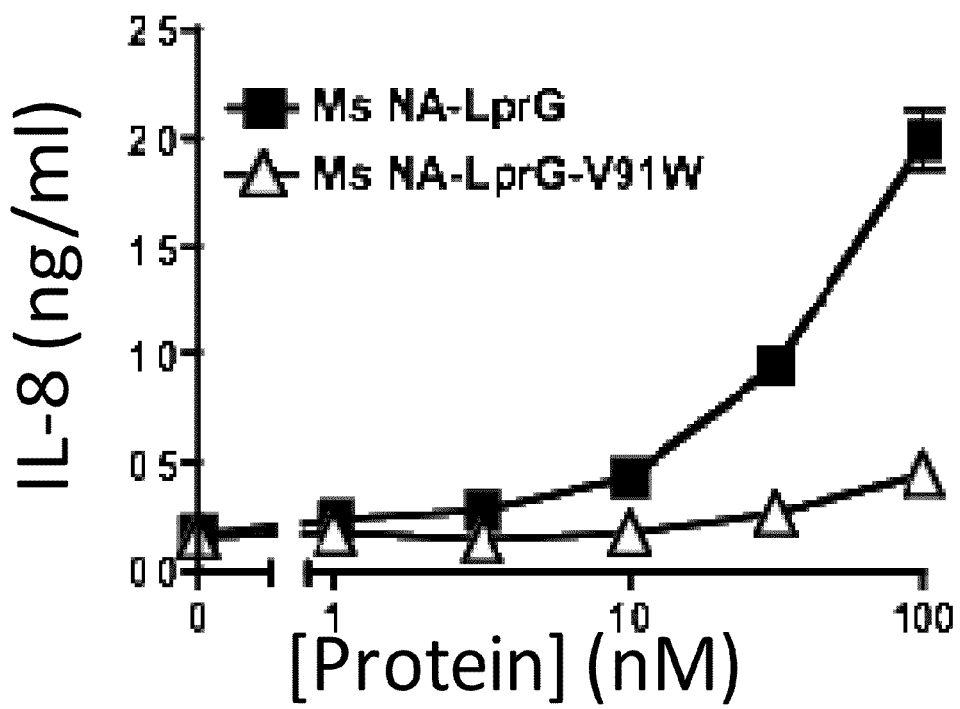
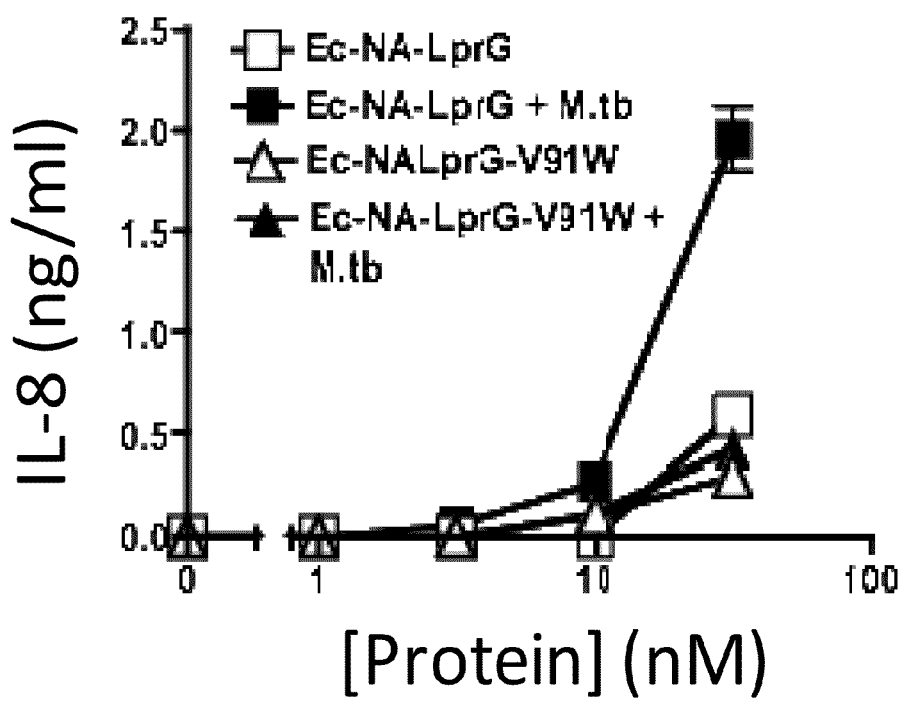
Fig. 3

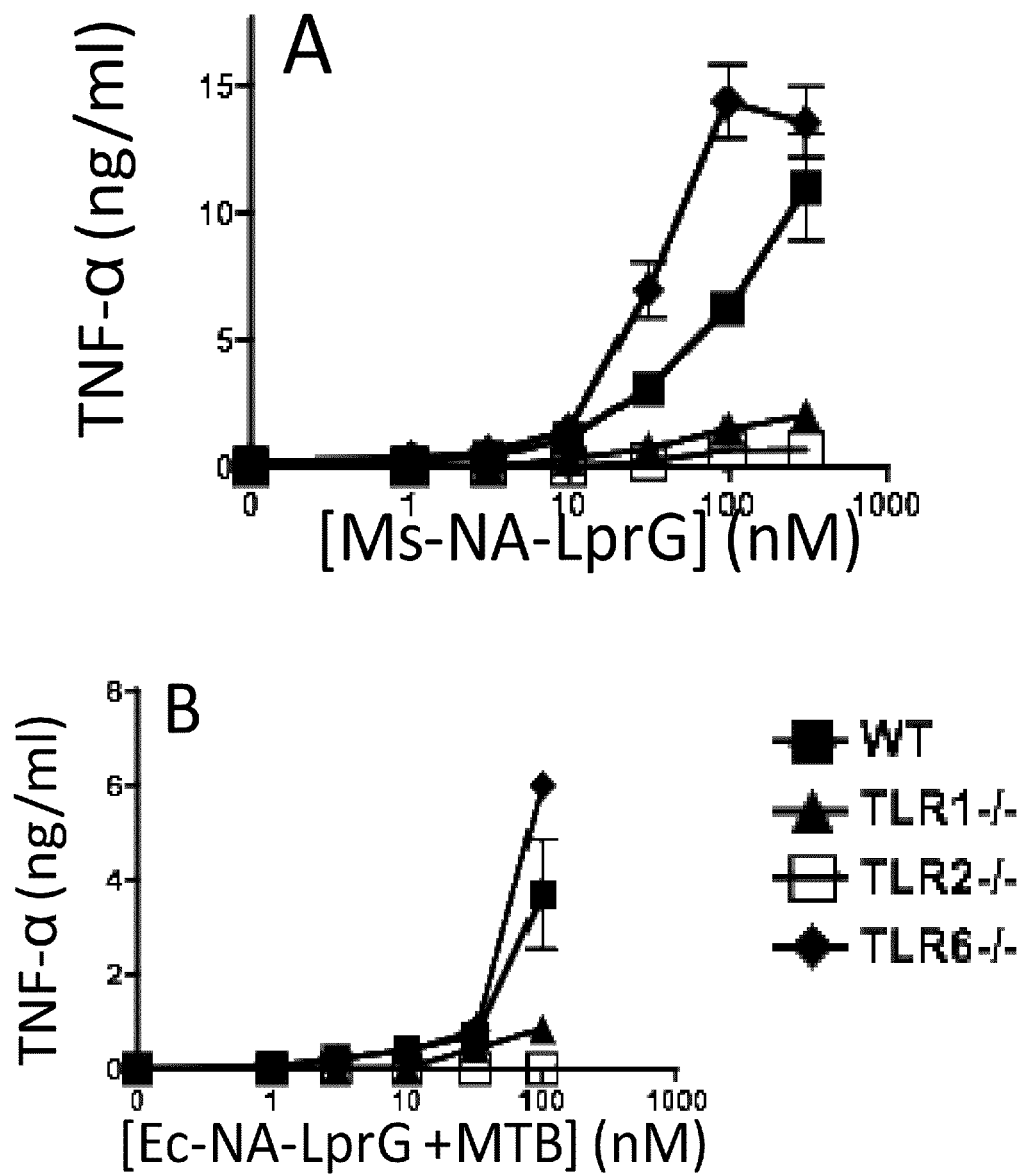
Fig. 4A-B

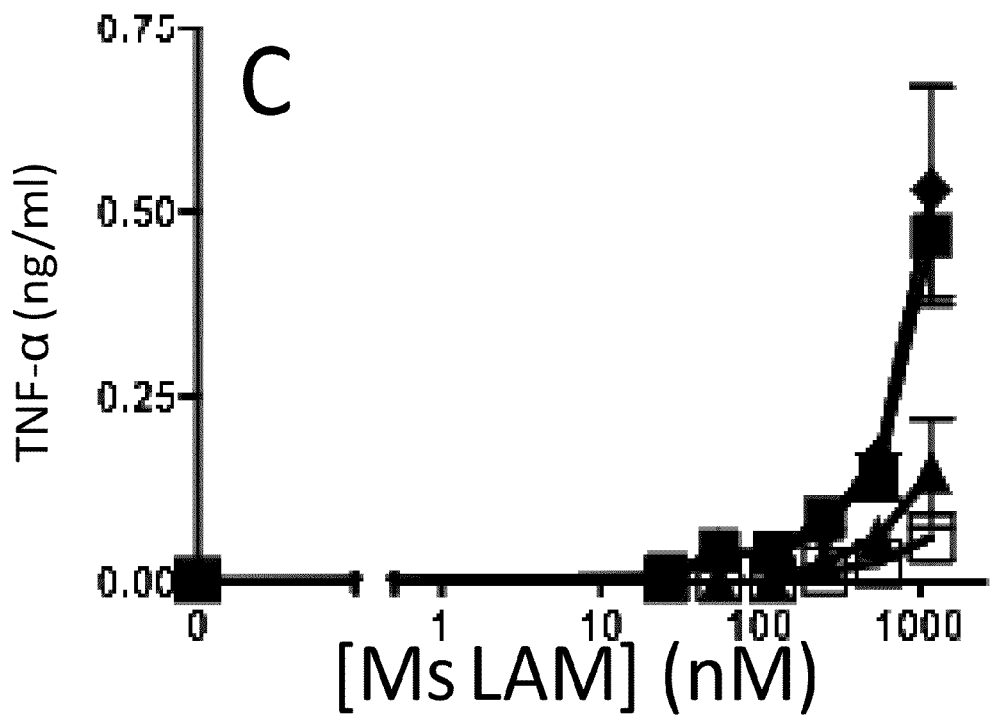
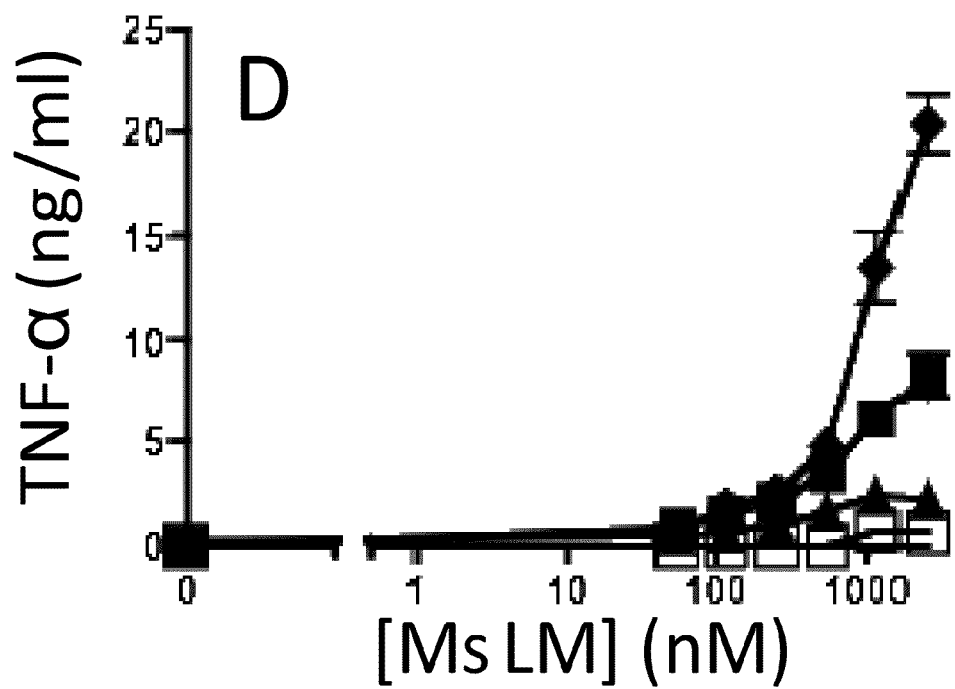
Fig. 4C-D

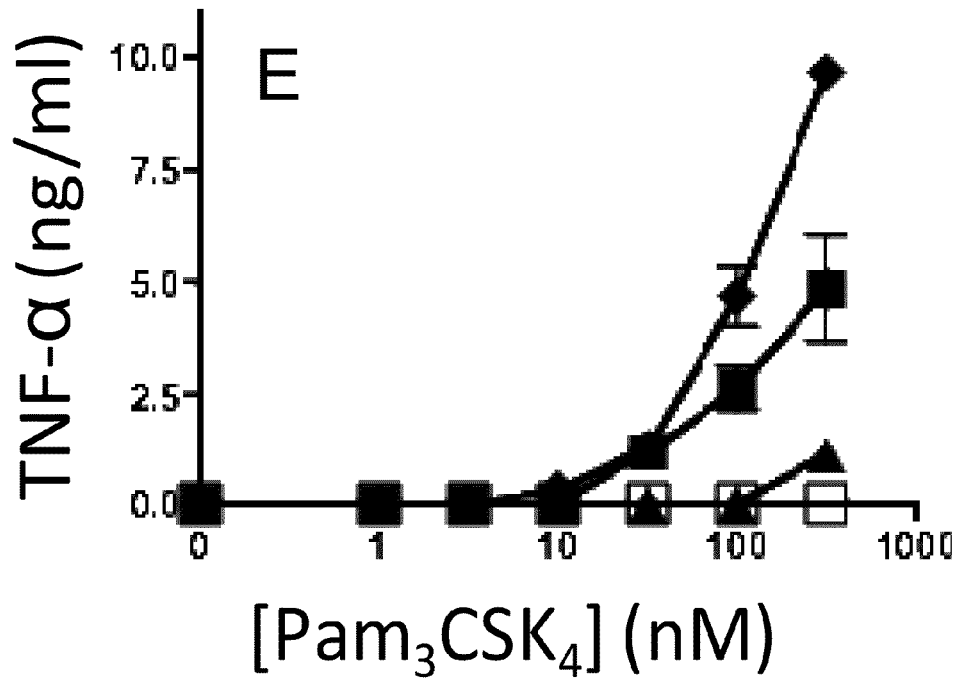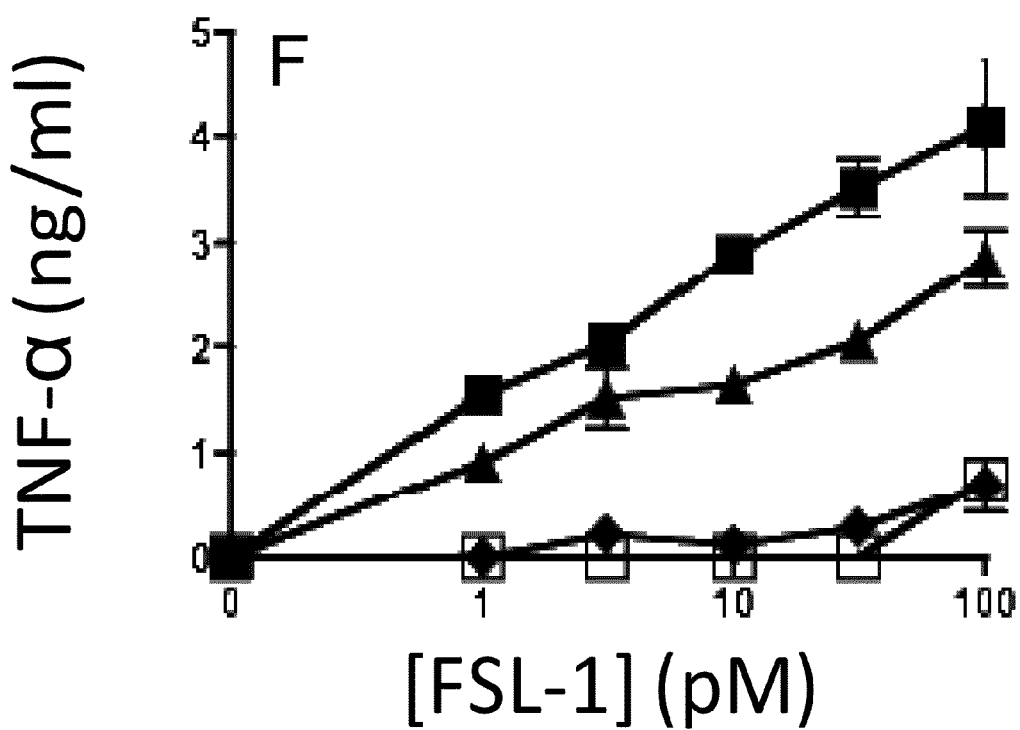
Fig. 4E-F

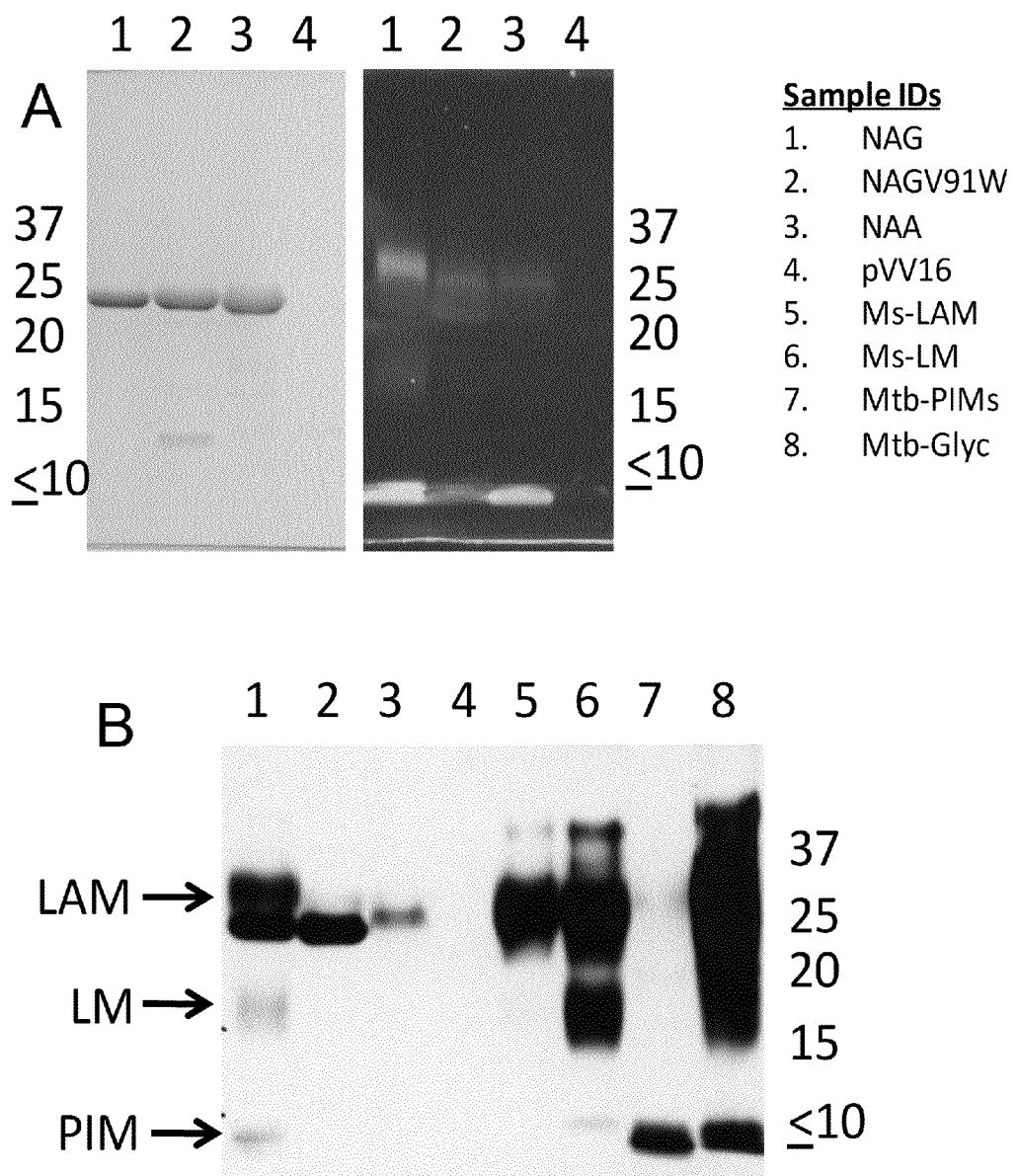
Fig. 5A-B

C

A: Silver stain (left), ProQ stain (right)
B: anti-BCG Western blot
C: anti-His$_6$ Western Blot

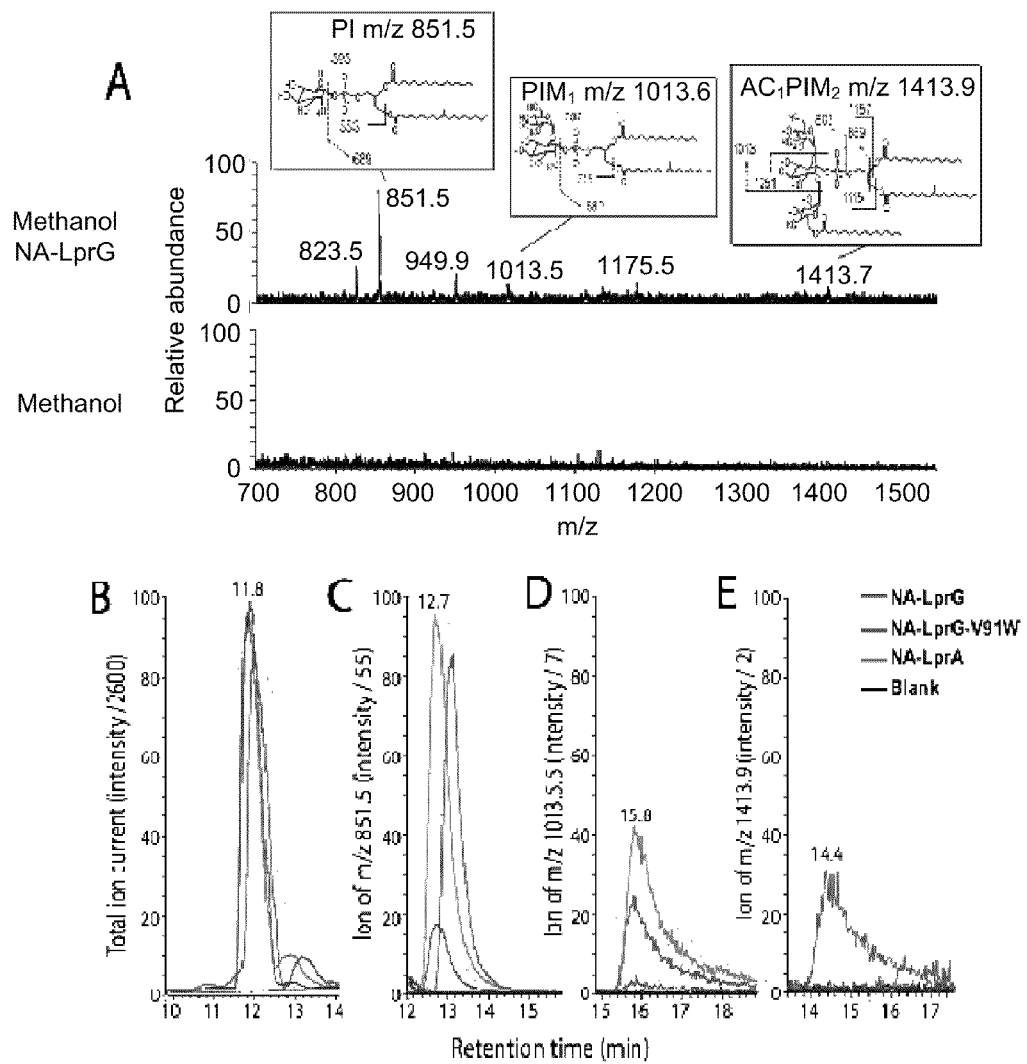
Fig. 6A-E

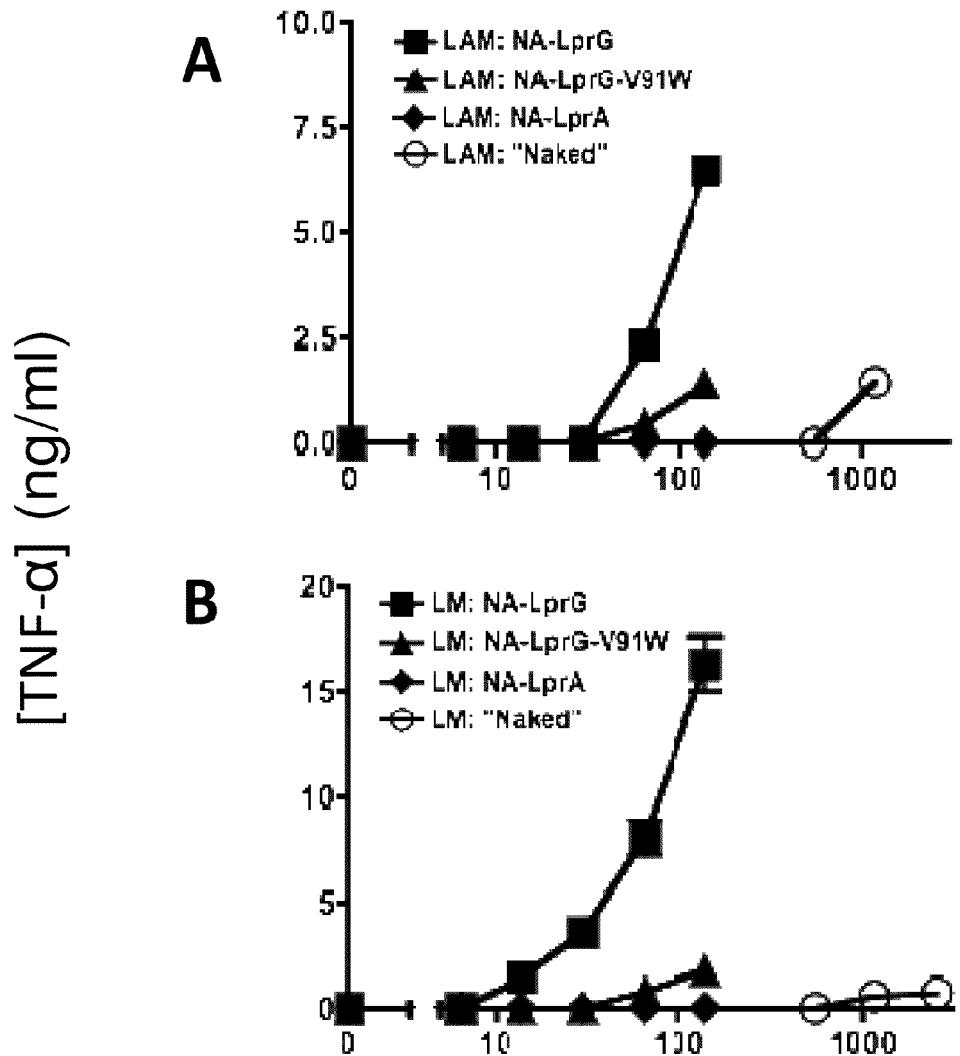
The values for the "naked" Glycolipids were on the edge of detection.
I expect the efficacy was actually much higher for LM,
So I am re-running the ELISA for these samples
to double-check.
Fig. 7A-B

US 8,404,251 B2

LPRG AS A CHAPERONE OF IMMUNE ADJUVANTS

RELATED APPLICATION

This application claims priority from U.S. Provisional Application No. 61/147,304, filed Jan. 26, 2009, the subject matter, which is incorporated herein by reference.

BACKGROUND

Immune adjuvants are molecules that signal through receptors to enhance immune responses. One example is the addition of adjuvants to vaccines to enhance the response to the vaccine antigens. The improvement of vaccine adjuvants is an important current goal in vaccine development. Adjuvants may also be important for other types of immunotherapy, including potential treatments under development for cancer, autoimmunity and other disorders in which the immune system may play a role in either pathophysiology or therapy.

Immune adjuvants may be derived from microbial molecules that generate responses in the mammalian recipient. Immune adjuvants are recognized by receptors, often in the category of innate immune receptors. One example of an innate immune receptor is the Toll-like receptor (TLR) family. TLRs recognize acylated molecules, such as lipoproteins, lipopeptides and glycolipids. TLRs can also respond to agonists by signaling to induce immune activation.

BRIEF SUMMARY OF THE INVENTION

The present invention relates to adjuvant combinations that stimulate immune activation. The adjuvant combinations include a hydrophobic immune adjuvant and a pathogen derived lipoprotein that chaperones the hydrophobic immune adjuvant to an immune receptor. In one aspect of the invention, the pathogen derived lipoprotein includes LprG.

In another aspect of the invention, the hydrophobic immune adjuvant is a glycolipid immune adjuvant. The hydrophobic immune adjuvant can also include at least one of a TLR agonist or TLR ligand. By way of example, the hydrophobic immune adjuvant can be at least one of a TLR2 agonist or TLR4 agonist.

The present invention also relates to an immune stimulating complex that includes a hydrophobic immune adjuvant and LprG. The LprG can be present in an amount effective to chaperone the immune adjuvant to an immune receptor. The hydrophobic immune adjuvant can be a glycolipid immune adjuvant. The hydrophobic immune adjuvant can also include at least one of a TLR2 agonist or TLR4 agonist.

The present invention further relates to a vaccine that includes a vaccine antigen, a hydrophobic TLR agonist, and LprG. The LprG can be provided in the vaccine in an amount effective to chaperone the hydrophobic TLR agonist to a TLR.

BRIEF DESCRIPTION OF THE DRAWINGS

FIG. 2 illustrates crystal structures of NA-LprG reveals a hydrophobic pocket with the potential to carry a TLR2 agonist.

FIG. 3 illustrates plots showing site-directed mutagenesis and single amino acid alteration of the hydrophobic pocket reduces the ability of NA-LprG to bind and deliver TLR2 agonists. (A) TLR2 Activity of NA-LprG and NA-LprG-V91W expressed in M. smegmatis and tested on HEK293.TLR2 cells as in FIG. 1. (B) TLR2 activity of NA-LprG and NA-LprG-V91W expressed in E. coli, purified, incubated with Mtb lysate and repurified as in FIG. 1F. Data for panels A and B are reported as the mean+/−SD of triplicate HEK293.TLR2 assays from a representative of at least 3 independent experiments.

FIG. 6 illustrates triacylated Ac$_1$PIM$_2$ is specifically associated with LprG. Nanospray ionization mass spectrometry in negative mode was used to analyze molecules associated with NA-LprG (A), NA-LprG-V91W (B) and NA-LprA (C).

FIG. 7 illustrates plots showing NA-LprG binds purified mycobacterial glycolipids and facilitates their recognition by TLR2. NA-LprG was purified from E. coli, incubated with preparations of PIM (containing a mixture of PIM$_1$/PIM$_2$ or PIM$_1$/PIM$_2$/PIM$_6$), LM from M. smegmatis, PI-LAM from M. smegmatis (Ms-LM and Ms-LAM, respectively), LM from Mtb H37Rv and ManLAM purified from Mtb H37Rv. NA-LprG was then repurified and assessed for TLR2 activity using HEK293.TLR2-CD14 cells as in FIG. 1. Data are reported as the mean+/−SD of triplicate HEK293.TLR2-CD14 assays from a representative of at least 3 independent experiments.

DETAILED DESCRIPTION

Figure 1A:
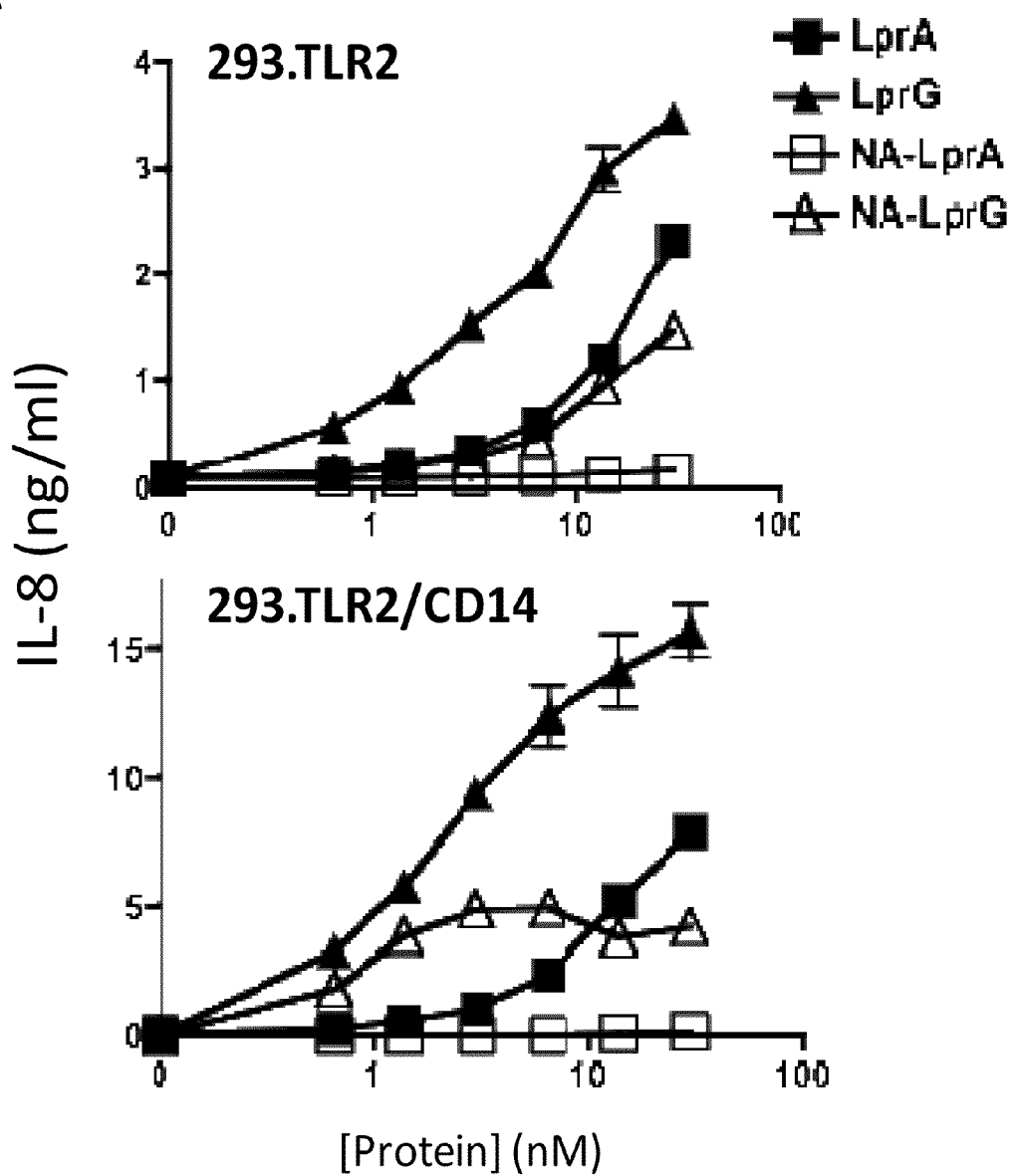
FIG. 1 illustrates NA-LprG carries a mycobacterial TLR2 agonist. (A) HEK293.TLR2 cells show a dose-dependent IL-8 response to LprA, LprG, and NA-LprG, but no response to NA-LprA. Top panel, bioassay with HEK293.TLR2 cells. Bottom panel, bioassay with HEK293.TLR2-CD14 cells. Control HEK293 cells lacking TLR2 and CD14 failed to respond to all four proteins, similar to the response seen to NA-LprA in these panels (data not shown). (B) Alignment of primary amino acid sequences of LprA (SEQ ID NO: 1) and LprG (SEQ ID NO: 2). Shared residues are highlighted. (C, D) TLR2 activity of NA-LprG/NA-LprA chimeric molecules. HEK293.TLR2 cells were incubated for 12 h with NA-LprG, NA-LprA or chimeric proteins combining the N-terminal half (NTD) and C-terminal half (CTD) of NA-LprG and NA-LprA. (E, F) NA-LprG can acquire TLR2 agonist activity from mycobacterial lysates. NA-LprG and NA-LprA were expressed in E. coli, purified, purified by Ni-affinity and ion exchange chromatography, incubated with control buffer or a lysate of M. smegmatis (E) or Mtb H37Ra (F), repurified by Ni-affinity and ion exchange chromatography, and incubated with HEK293.TLR2 cells for 12 h. For all data panels, IL-8 production was quantified by ELISA, and data are reported as the mean+/−SD of triplicate HEK293.TLR2 assays from a representative of at least 3 independent experiments.
Figure 4G:
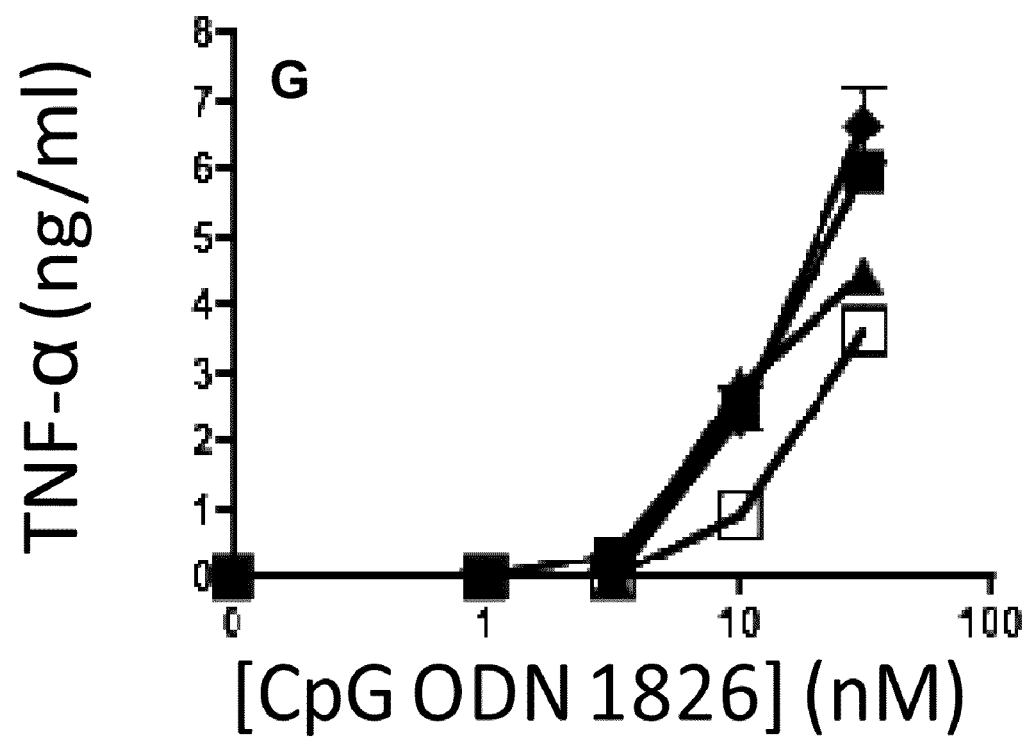
FIG. 4 illustrates plots showing NA-LprG activity is dependent on TLR1 and TLR2. (A, B) Macrophage response to NA-LprG is dependent on TLR2 and TLR1, but not dependent on TLR6. NA-LprG was purified from M. smegmatis (panel A) or purified from E. coli, incubated with Mtb H37Ra lysate and then repurified (panel B). NA-LprG preparations were incubated for with bone marrow-derived macrophages from TLR2−/−, TLR1−/−, TLR6−/− or wild-type mice, and TNF-alpha production was determined by ELISA. (C-D) Macrophage responses to mycobacterial glycolipids are dependent on TLR2 and TLR1, but not dependent on TLR6. TLR dependency was assessed as above. (E, F). TLR2 responses to triacylated and diacylated lipopeptides are dependent on TLR1 and TLR6, respectively. (G) Response to non-TLR2 signaling (by CpG ODN 1826 TLR9 agonist) is intact in knockout cell lines. Data are reported as the mean+/−SD of triplicate macrophage assays from a representative of at least 3 independent experiments.

The present invention relates to pathogen derived lipoprotein formulations (e.g., LprG formulations) that unexpectedly can be used as efficient delivery vehicles for hydrophobic immune adjuvants, such as hydrophobic TLR ligands. It was found that pathogen derived lipoprotein formulations are a particularly effective vehicle for delivery of hydrophobic immune adjuvants, such as TLR ligands, particularly those that would be immunologically inert or poorly immunostimulatory if not administered together with the pathogen derived lipoprotein formulations. Although not intending to be bound by any particular mechanism, it is postulated that the pathogen derived lipoprotein formulations enhance delivery of such ligands to their respective receptors (e.g., particular TLR family members) by complexing with or binding to the hydrophobic immune adjuvants and chaperoning the immune adjuvant to the desired immune receptor. This has resulted in the observed synergistic enhancement of innate immune responses when the ligand/lipoprotein formulation is used in particular experimental therapeutic settings.

It was unexpected that use of pathogen derived lipoprotein formulations of the present invention could essentially chaperone previously-characterized immunologically substantially inert hydrophobic TLR ligands to TLR to stimulate an immune response. This observation broadens the genus of TLR ligands that can be used for immunostimulatory purposes to include TLR ligands with no previously characterized immunostimulatory motif and/or no or low previously characterized immunostimulatory potential.

These findings indicate that adjuvant combinations comprising pathogen derived lipoprotein formulations and hydrophobic immune adjuvants are useful in optimizing innate immune therapies, such as but not limited to those directed to infectious disease, cancers, allergy and asthma.

In one aspect of the invention, the pathogen derived lipoprotein can include an LprG lipoprotein that is derived from *Mycobacterium tuberculosis* (Mtb) and that can chaperone a hydrophobic immune adjuvant to an immune receptor. It was found that acylated LprG and non-acylated LprG can act as a myobacterial glycolipid chaperone and deliver the glycopids for recognition by TLRs (e.g., TLR-2).

In another aspect of the invention, the hydrophobic immune adjuvant can include a glycolipid adjuvant, such as a pathogen-derived (e.g., *Myobacterium*) glycolipid adjuvant. In general terms, an adjuvant is a substance that non-specifically enhances the immune response to an antigen, i.e., is an immunostimulant. In general terms, a glycolipid is a cell membrane lipid molecule with a carbohydrate chain attached to a hydrophobic tail. Glycolipid adjuvants of the present invention can include modified lipopolysaccharides. The lipopolysaccharide is modified such that its toxicity is reduced compared to the corresponding wild type lipopolysaccharide or lipopolysaccharide from which it has been derived.

In one example, the glycolipid immune adjuvant can be a hydrophobic TLR ligand and/or a hydrophobic TLR agonist. The hydrophobic TLR ligand and/or hydrophobic TLR agonist can be formulated with the pathogen derived lipoprotein in any number of ways. For example, the TLR ligand and/or TLR agonist can simply be mixed with the pathogen derived lipoproteins.

As used herein, a TLR ligand is a molecule that binds to a TLR (i.e., a Toll-like receptor). There are a number of TLR identified to date including TLR1, TLR2, TLR3, TLR4, TLR5, TLR6, TLR7, TLR8, TLR9, TLR10 and TLR11. There are similarly a number of TLR ligands identified to date, some of which have been observed to be immunostimulatory (e.g., CpG oligonucleotides). The invention intends to embrace hydrophobic TLR ligands that have been previously identified as being TLR ligands and which may have also been observed to be immunologically inert. As used herein, an immunologically inert TLR ligand is one which has been observed to have no or low immunostimulatory potential. The invention also intends to embrace compounds that according to the invention are tested in the presence and absence of a pathogen derived lipoprotein (e.g., LprG) and found to be transformed from an inert compound to an immunostimulatory compound.

Screening assays for TLR ligands have been described in, for example, U.S. Patent Application Publication No. US 2003/0104523, published Jun. 5, 2003, which is incorporated herein in their entirety. The invention intends to embrace the use of compounds that are shown to be TLR ligands (e.g., via radiolabeled ligand-receptor assays) but which when compared to, for example, immunostimulatory adjuvants appear to be inert because their relative immunostimulatory potential is negligible or therapeutically non-useful in comparison.

The adjuvant combinations comprising the pathogen derived lipoprotein and hydrophobic immune adjuvants can further include an antigen for inducing an immunological response in a mammal (e.g., human). The antigen can be provided with the adjuvant combinations in a vaccine that can be inoculated in an individual to produce antibody, preferably IgA, and/or a T cell immune response. The response can be adequate to protect said individual from infection, particularly bacterial or viral infection. Thus, the immunological response may be used therapeutically or prophylatically.

The vaccine antigen can include but is not limited to bacterial, viral, parasitic, allergens, autoantigens and tumor associated antigens. Particularly, the antigen can include protein antigens, peptides, whole inactivated organisms, and the like.

Specific examples of antigens that can be used in the invention include antigens from hepatitis A, B, C or D, influenza virus, *Listeria, Clostridium botulinum*, tuberculosis, tularemia, Variola major (smallpox), viral hemorrhagic fevers, *Yersinia pestis* (plague), HIV, herpes, pappilloma virus, and other antigens associated with infectious agents. Other antigens include antigens associated with a tumor cell, antigens associated with autoimmune conditions, allergy and asthma. Administration of such an antigen in conjunction with the subject immune combination can be used in a therapeutic or prophylactic vaccine for conferring immunity against such disease conditions.

In some embodiments, the methods and compositions can be used to treat an individual at risk of having an infection or has an infection by including an antigen from the infectious agent. An infection refers to a disease or condition attributable to the presence in the host of a foreign organism or an agent, which reproduce within the host. A subject at risk of having an infection is a subject that is predisposed to develop an infection. Such an individual can include for example a subject with a known or suspected exposure to an infectious organism or agent. A subject at risk of having an infection can also include a subject with a condition associated with impaired ability to mount an immune response to an infectious agent or organism, for example a subject with a congenital or acquired immunodeficiency, a subject undergoing radiation or chemotherapy, a subject with a burn injury, a subject with a traumatic injury, a subject undergoing surgery, or other invasive medical or dental procedure, or similarly immunocompromised individual.

Infections which may be treated or prevented with the vaccine compositions of this invention include bacterial, viral, fungal, and parasitic. Other less common types of infection also include are rickettsiae, mycoplasms, and agents causing scrapie, bovine spongiform encephalopathy (BSE), and prion diseases (e.g., kuru and Creutzfeldt-Jacob disease). Examples of bacteria, viruses, fungi, and parasites that infect humans are well know. An infection may be acute, subacute, chronic or latent and it may be localized or systemic. Furthermore, the infection can be predominantly intracellular or extracellular during at least one phase of the infectious organism's agent's life cycle in the host.

Bacteria infections against which the subject vaccines and methods may be used include both Gram negative and Gram positive bacteria. Examples of Gram positive bacteria include but are not limited to *Pasteurella* species, Staphylococci species, and Streptococci species. Examples of Gram negative bacteria include but are not limited to *Escherichia coli, Pseudomonas* species, and *Salmonella* species. Specific examples of infectious bacteria include but are not limited to *Heliobacter pyloris, Borrelia burgdorferi, Legionella pneumophilia, Mycobacteria* spp. (for example *M. tuberculosis, M. avium, M. intracellilare, M. kansaii, M. gordonae*), *Staphylococcus aureus, Neisseria gonorrhoeae, Neisseria meningitidis, Listeria monocytogeners, Streptococcus pyogenes*, (group A *Streptococcus*), *Streptococcus agalactiae* (Group B *Streptococcus*), *Streptococcus* (viridans group), *Streptococcus faecalis, streptococcus bovis, Streptococcus* (anaerobic spp.), *Streptococcus pneumoniae*, pathogenic *Campylobacter* spp., *Enterococcus* spp., *Haemophilus influenzae, Bacillus anthracis, Corynebacterium diptheriae, Corynebacterium* spp., *Erysipelothrix rhusiopathie, Clostridium perfringens, Clostridium tetani, Enterobacter aerogenes, Klebsiella pneumoniae, Pasteurella multocida, Bacteroides* spp., *Fusobacterium nucleatum, Streptobacillus moniliformis, Treponema pallidum, Treponema pertenue, Leptospira, Rickettsia*, and *Actinomyces israelii*.

Examples of viruses that cause infections in humans include but are not limited to Retroviridae (for example human deficiency viruses, such as HIV-1 (also referred to as HTLV-III), HIV-II, LAC or IDLV-III (LAV or HIV-III and other isolates such as HIV-LP, Picornaviridae (for example poliovirus, hepatitis A, enteroviruses, human Coxsackie viruses, rhinoviruses, echoviruses), Calciviridae (for example strains that cause gastroenteritis), Togaviridae (for example equine encephalitis viruses, rubella viruses), Flaviviridae (for example dengue viruses, encephalitis viruses, yellow fever viruses) Coronaviridae (for example coronaviruses), Rhabdoviridae (for example vesicular stomata viruses, rabies viruses), Filoviridae (for example Ebola viruses) Paramyxoviridae (for example parainfluenza viruses, mumps viruses, measles virus, respiratory syncytial virus), Orthomyxoviridae (for example influenza viruses), Bungaviridae (for example Hataan viruses, bunga viruses, phleoboviruses, and Nairo viruses), Arena viridae (hemorrhagic fever viruses), Reoviridae (for example reoviruses, orbiviruses, rotaviruses), Bimaviridae, Hepadnaviridae (hepatitis B virus), Parvoviridae (parvoviruses), Papovaviridae (papilloma viruses, polyoma viruses), Adenoviridae (adenoviruses), Herpeviridae (for example herpes simplex virus (HSV) I and II, varicella zoster virus, pox viruses) and Iridoviridae (for example African swine fever virus) and unclassified viruses (for example the etiologic agents of Spongiform encephalopathies, the agent of delta hepatitis, the agents of non-A, non-B hepatitis (class 1 enterally transmitted; class 2 parenterally transmitted such as Hepatitis C); Norwalk and related viruses and astroviruses).

Examples of fungi include *Aspergillus* spp., *Coccidoides immitis, Cryptococcus neoformans, Candida albicans* and other *Candida* spp., *Blastomyces dermatidis, Histoplasma capsulatum, Chlamydia trachomatis, Nocardia* spp., and *Pneumocytis carinii*.

Parasites include but are not limited to blood-borne and/or tissue parasites such as *Babesia microti, Babesi divergans, Entomoeba histolytica, Giarda lamblia, Leishmania tropica, Leishmania* spp., *Leishmania braziliensis, Leishmania donovdni, Plasmodium falciparum, Plasmodium malariae, Plasmodium ovale, Plasmodium vivax, Toxoplasma gondii, Trypanosoma gambiense* and *Trypanosoma* rhodesiense (African sleeping sickness), *Trypanosoma cruzi* (Chagus' disease) and *Toxoplasma gondii*, flat worms, and round worms.

The present invention further embraces the use of the subject adjuvant combinations in treating proliferative diseases, such as cancers. Cancer is a condition of uncontrolled growth of cells, which interferes with the normal functioning of bodily organs and systems. A subject that has a cancer is a subject having objectively measurable cancer cells present in the subjects' body. A subject at risk of developing cancer is a subject predisposed to develop a cancer, for example based on family history, genetic predisposition, subject exposed to radiation or other cancer-causing agent. The adjuvant combinations and compositions according to the invention can be used to treat a variety of cancers or subjects at risk of developing cancer, by the inclusion of a tumor-associated-antigen (TAA). Examples of such cancers include breast, prostate, colon, blood cancers such as leukemia, chronic lymphocytic leukemia, and the like. The vaccination methods of the invention can be used to stimulate an immune response to treat a tumor by inhibiting or slowing the growth of the tumor or decreasing the size of the tumor. A tumor associated antigen can also be an antigen expressed predominantly by tumor cells but not exclusively.

Additional cancers include but are not limited to basal cell carcinoma, biliary tract cancer, bladder cancer, bone cancer, brain and central nervous system (CNS) cancer, cervical cancer, choriocarcinoma, colorectal cancers, connective tissue cancer, cancer of the digestive system, endometrial cancer, esophageal cancer, eye cancer, head and neck cancer, gastric cancer, intraepithelial neoplasm, kidney cancer, larynx cancer, liver cancer, lung cancer (small cell, large cell), lymphoma including Hodgkin's lymphoma and non-Hodgkin's lymphoma; melanoma; neuroblastoma; oral cavity cancer (for example 11p, tongue, mouth and pharynx); ovarian cancer; pancreatic cancer; retinoblastoma; rhabdomyosarcoma; rectal cancer; cancer of the respiratory system; sarcoma; skin cancer; stomach cancer; testicular cancer; thyroid cancer; uterine cancer; cancer of the urinary system; as well as other carcinomas and sarcomas.

The adjuvant combinations and compositions containing according to the invention can also be used to treat autoimmune diseases such as multiple sclerosis, rheumatoid arthritis, type 1 diabetes, psoriasis or other autoimmune disorders. Other autoimmune disease which potentially may be treated with the vaccines and immune adjuvants of the invention include Crohn's disease and other inflammatory bowel diseases such as ulcerative colitis, systemic lupus eythematosus (SLE), autoimmune encephalomyelitis, myasthenia gravis (MG), Hashimoto's thyroiditis, Goodpasture's syndrome, pemphigus, Graves disease, autoimmune hemolytic anemia, autoimmune thrombocytopenic purpura, scleroderma with anti-collagen antibodies, mixed connective tissue disease, polypyositis, pernicious anemia, idiopathic Addison's disease, autoimmune associated infertility, glomerulonephritis) for example crescentic glomerulonephritis, proliferative glomerulonephritis), bullous pemphigoid, Sjogren's syndrome, psoriatic arthritis, insulin resistance, autoimmune diabetes mellitus (type 1 diabetes mellitus; insulin dependent diabetes mellitus), autoimmune hepatitis, autoimmune hemophilia, autoimmune lymphoproliferative syndrome (ALPS), autoimmune hepatitis, autoimmune hemophilia, autoimmune lymphoproliferative syndrome, autoimmune uveoretinitis, and Guillain-Bare syndrome. Recently, arteriosclerosis and Alzheimer's disease have been recognized as autoimmune diseases. Thus, in this embodiment of the invention the antigen will be a self-antigen against which the host elicits an unwanted immune response that contributes to tissue destruction and the damage of normal tissues.

The adjuvant combinations and compositions containing according to the invention can also be used to treat asthma and allergic and inflammatory diseases. Asthma is a disorder of the respiratory system characterized by inflammation and narrowing of the airways and increased reactivity of the airways to inhaled agents. Asthma is frequently although not exclusively associated with atopic or allergic symptoms. Allergy is acquired hypersensitivity to a substance (allergen). Allergic conditions include eczema, allergic rhinitis, or coryza, hay fever, bronchial asthma, urticaria, and food allergies and other atopic conditions. An allergen is a substance that can induce an allergic or asthmatic response in a susceptible subject. There are numerous allergens including pollens, insect venoms, animal dander, dust, fungal spores, and drugs.

Examples of natural and plant allergens include proteins specific to the following genera: *Canine, Dermatophagoides, Felis, Ambrosia, Lotium, Cryptomeria, Alternaria, Alder, Alinus, Betula, Quercus, Olea, Artemisia, Plantago, Parietaria, Blatella, Apis, Cupressus, Juniperus, Thuya, Chamaecyparis, Periplanet, Agopyron, Secale, Triticum, Dactylis, Festuca, Poa, Avena, Holcus, Anthoxanthum, Arrhenatherum, Agrostis, Phleum, Phalaris, Paspalum, Sorghum*, and *Bromis*.

It is understood that the adjuvant combinations and compositions containing according to the invention can be combined with other therapies for treating the specific condition, e.g., infectious disease, cancer or autoimmune condition. For example in the case of cancer the inventive methods may be combined with chemotherapy or radiotherapy.

The adjuvant combinations of the invention can be administered locally or systemically by any method known in the art including but not limited to intramuscular, intravenous, intradermal, subcutaneous, intraperitoneal, intranasal, oral or other mucosal routes. Additional routes include intracranial (for example intracisternal, or intraventricular), intraorbital, ophthalmic, intracapsular, intraspinal, and topical administration. The adjuvants and vaccine compositions of the invention can be administered in a suitable, nontoxic pharmaceutical carrier, or can be formulated in microcapsules or a sustained release implant. The immunogenic compositions of the invention can be administered multiple times, if desired, in order to sustain the desired cellular immune response. The appropriate route, formulation, and immunization schedule can be determined by one skilled in the art.

The subject adjuvant combinations can be administered with a physiologically acceptable carrier such as physiological saline. The composition may also include another carrier or excipient such as buffers, such as citrate, phosphate, acetate, and bicarbonate, amino acids, urea, alcohols, ascorbic acid, phospholipids, proteins such as serum albumin, ethylenediamine tetraacetic acid, sodium chloride or other salts, liposomes, mannitol, sorbitol, glycerol and the like. The adjuvants of the invention can be formulated in various ways, according to the corresponding route of administration. For example, liquid formulations can be made for ingestion or injection, gels or procedures can be made for ingestion, inhalation, or topical application. Methods for making such formulations are well known and can be found in for example, "Remington's Pharmaceutical Sciences," 18.sup.th Ed., Mack Publishing Company, Easton Pa.

It is understood that modifications which do not substantially affect the activity of the various embodiments of this invention are also provided within the definition of the invention provided herein. The various references to journals, patents, and other publications which are cited herein comprise the state of the art and are incorporated by reference as though fully set forth.

EXAMPLES

To investigate the roles of acyl chains and other potential determinants in TLR2 agonist activity of Mtb lipoproteins, we expressed nonacylated (NA) variants of LprA and LprG, termed NA-LprA and NA-LprG, respectively. While NA-LprA appeared to lose its TLR2 stimulatory activity, NA-LprG retained TLR2 stimulatory capacity. The crystal structure of NA-LprG revealed a putative binding pocket lined with hydrophobic residues, and biochemical studies revealed binding of triacylated Mtb glycolipids to NA-LprG. Mutation of the putative binding pocket reduced TLR2 agonist activity of acylated LprG and selectively abolished the ability of NA-LprG to bind triacylated phospholipids. These results present two new interpretations. First, we show that the evolutionary function of LprG in mycobacteria is to act as a glycolipid chaperone to mediate trafficking and delivery of glycolipid during construction of the mycobacterial envelope, contributing to virulence and providing potential opportunities for targeting in drug design. Second, we show that a glycolipid chaperone activity of LprG facilitates recognition of triacylated glycolipids by TLR2. This presents a novel paradigm for recognition of hydrophobic TLR2 agonists that require chaperones for delivery to TLR2; host cells may co-opt the function of microbial chaperones, providing a mechanism to enhance innate immune recognition of Mtb or other bacteria that express hydrophobic TLR2 agonists.

Having previously determined that purified wild-type LprG and LprA proteins activate TLR2, we sought to determine whether the mechanism involved triacylation at the N-terminal cysteine. Since acylation of these lipoproteins is mediated by a common enzymatic pathway, we investigated whether the protein structure of these lipoproteins could contribute to TLR2 agonist activity independent of the presence of the N-terminal cysteine required for tri-acylation. Recombinant 6×His-tagged acylated and non-acylated versions of LprA and LprG were expressed and assessed for TLR2 activity (non-acylated forms were expressed without the leader peptide and with the acylated N-terminal cysteine replaced with methionine). Mtb LprG was a more potent TLR2 agonist than a homologous Mtb lipoprotein, LprA, in a bioassay with TLR2-transfected HEK293.TLR2 cells. NA-LprA did not induce TLR2 responses implicating the tri-acyl motif in its mechanisms of action. However, NA-LprG retained significant TLR2 agonist activity (lower than acylated LprG but as high or higher than acylated LprA) (FIG. 1A). Interestingly, expression of CD14 (in HEK293.TLR2-CD14 cells) enhanced the apparent potency of NA-LprG but not acylated LprG or LprA (FIG. 1A), consistent with other evidence that the mechanism for recognition of the NA-LprG-associated TLR2 agonist activity was different than for acylated LprG and LprA (below). These data indicate that determinants other than acylation of the N-terminal cysteine contribute to TLR2 agonist activity of LprG.

To test whether specific peptide sequences or domains were required for TLR2 agonist activity of NA-LprG, we produced N-terminal truncation mutants of NA-LprG. Truncations within the first 14 amino acids did not affect TLR2 agonist activity, and further truncation involving the first alpha helix by subsequent structural studies, produced instability and poor expression (data not shown). Since LprG and LprA are homologous (FIG. 1B), and LprA lacks acyl-independent TLR2 activity, an alternative strategy was to produce full-length chimeric molecules containing different portions of LprG and LprA to determine which portions of LprG conferred TLR2 activity. Chimeric molecules were produced containing the N-terminal half of NA-LprA and the C-terminal half of NA-LprG, or vice versa, and tested for TLR2 agonist activity with HEK293.TLR2 cells (FIG. 1C, D). Both chimeric molecules were active, although greater activity was associated with LprG sequence in the C-terminal domain, suggesting that both halves of the molecule contributed to agonism, perhaps through a conformational determinant.

Since a closely related lipoprotein, LppX, is thought to bind and transport hydrophobic phthiocerol dimycocerosates, we hypothesized that LprG might non-covalently bind a lipid TLR2 agonist via a conformation-dependent binding site. This hypothesis was supported by the observation that NA-LprG had reduced activity when expressed in E. coli instead of M. smegmatis (FIG. 1E), suggesting that TLR2 agonist(s) carried by LprG may be specific to mycobacteria. Further suggesting non-covalent capture of a cell wall product, the activity of NA-LprG purified from E. coli was significantly increased following incubation with lysates of either M. smegmatis (FIG. 1E) or Mtb H37Ra (FIG. 1F). Similar charging of TLR2 agonist activity of NA-LprG from E. coli was observed with lysate from Mtb H37Rv demonstrating that the effect is relevant to virulent Mtb. These results suggest that NA-LprG binds mycobacterial TLR2 agonist(s) and delivers them for recognition by TLR2.

To test the hypothesis that the hydrophobic pocket of LprG serves as a binding site, we performed site-directed mutagenesis to create a V91W mutant, replacing a valine lining the interior pore with a bulky tryptophan. NA-LprG-V91W was stably expressed in M. smegmatis, and its ability to activate TLR2 was significantly reduced relative to NA-LprG expressed in M. smegmatis (FIG. 3) Mutations at other sites (V194R and V217F) also decreased TLR2 agonist activity of NA-LprG (data not shown). Furthermore, when NA-LprG-V91W was expressed in E. coli, purified and then incubated with a sonicate of M. smegmatis or Mtb, the V91W mutant lacked the ability to acquire TLR2 agonist activity from mycobacteria (FIG. 3) and data not shown). These results provide strong support for the hypothesis that the hydrophobic cavity serves as a binding site for TLR2 agonist(s), which are then delivered by LprG for recognition by TLR2.

Since TLR2 co-receptor dependence varies with different types of TLR2 agonists, we investigated properties of TLR2 agonist(s) putatively associated with NA-LprG by testing the dependence of NA-LprG signaling on TLR2 co-receptors, TLR1 and TLR6. NA-LprG from *M. smegmatis* was incubated with bone marrow-derived macrophages from mice genetically deficient in TLR1, TLR2 or TLR6, and TNFα production was quantified by ELISA. Recognition of NA-LprG or associated molecules was deficient in TLR2$^{-/-}$ and TLR1$^{-/-}$ macrophages but not TLR6$^{-/-}$ macrophages (FIG. 4A). Similar results were observed with NA-LprG that was expressed in *E. coli* and then incubated with Mtb lysate to allow loading of NA-LprG with Mtb-derived TLR2 agonist(s) (FIG. 4B). These results suggest that the activity associated with NA-LprG signals through TLR2/TLR1 heterodimers, similar to the mycobacterial glycolipids LAM (FIG. 4C), LM (FIG. 4D) as well as triacylated lipopeptide (FIG. 4E). In contrast, the diacylated lipopeptide FSL-1 was dependent on TLR2 and TLR6, but not TLR1 (FIG. 4F). All macrophage types responded to CpG ODN 1826, a TLR9 agonist, confirming responsiveness of these cells to other TLR stimuli (FIG. 4G). Other studies with macrophages from CD14$^{-/-}$ mice showed that NA-LprG activity was dependent on CD14 (data not shown), consistent with observations that CD14 contributes to TLR2 recognition of triacylated lipopeptides and glycolipids. The dependence of NA-LprG and Mtb glycolipid signaling on TLR2/TLR1 and CD14 suggests that putative TLR2 agonist(s) associated with NA-LprG have recognition requirements similar to triacylated mycobacterial glycolipids, including LM and LAM (and consistent with TLR2-dependent, TLR6-independent activity of PIM6).

To directly identify molecules that non-covalently associate with NA-LprG, proteins were purified from *M. smegmatis* by and subjected to SDS-PAGE with silver stain, Pro-Q stain for carbohydrates following periodate oxidation (see Methods), or Western blot using a monoclonal anti-His$_6$ antibody or a polyclonal anti-*M. bovis* BCG antibody that recognizes many components of BCG and Mtb (FIG. 5). Silver stain and anti-His$_6$ Western of protein preparations showed an isolated band at approximately 24 kDa representing NA-LprG, NA-LprG-V91W or NA-LprA (FIG. 5A). The Pro-Q carbohydrate stain showed diffuse bands with apparent molecular weights of 25-35 kDa, 14-18 kDa and 8-9 kDa (FIG. 5A, right panel), which correspond to the apparent molecular weights by SDS-PAGE of Mtb glycolipids LAM, LM and PIM, respectively (FIG. 5B). These compounds are likely glycolipids because they were seen after peroxidation but not on conventional silver stain, and glycolipids in the PIM-LAM series resolve as broad bands based on heterogeneity of the arabinose and mannan components in each molecular species. Importantly, the bands corresponding to LAM and LM were more prominent with NA-LprG than NA-LprG-V91W or LprA, suggesting that these glycolipids, which are predominantly tri-acylated, are associated preferentially with NA-LprG with little or no association with NA-LprG-V91W or NA-LprA. PIM was associated with all three proteins, possibly related to its existence in multiple states of acylation, including diacylated as well as triacylated forms (below). The polyclonal anti-BCG antibody detected NA-LprG and bands with apparent molecular weights consistent with the LAM and LM (FIG. 5); monoclonal antibody to LAM stained the higher molecular weight band (data not shown). These results provided evidence for Mtb glycolipid association with NA-LprG but not NA-LprG-V91W or NA-LprA. Of note, LAM and LM share a common core of triacylated PIM (although other PIM acylation variants exist), suggesting that all of these mycobacterial glycolipids associate with NA-LprG and signal through TLR2/TLR1 via a shared structural motif.

To directly determine the molecular structures of small molecules associated with LprG and related proteins, we treated proteins with methanol to denature and solubilize lipids. We then analyzed methanol eluates with nanoelectrospray ionization mass spectrometry to detect compounds with a mass to charge (m/z) up to 2000. Methanol alone (FIG. 6A) or methanol elutes of an unrelated protein Pab C (not shown) did not give detectable ions. In contrast, both LprG (not shown) and NA-LprG (FIG. 6A) expressed in *M. smegmatis* yielded ions corresponding to mycobacterial phospholipids. Ions detected at m/z 851.4, 1013.5, 1175.5 and 1413.7 corresponded in mass to [M-H]− of phosphatidylinositol, diacyl phosphatidylinositol monomannoside ($PIM_1$), diacyl $PIM_2$ and triacyl $PIM_2$, respectively. Collision induced dissociation mass spectrometry (CID-MS) analysis of these compounds yielded product ions expected from these assigned molecules, confirming the tentative assignments of these compounds (FIG. 6A upper panels). For example, triacyl $Ac_1PIM2$ (m/z 1413.7) yielded products corresponding to the loss of mannose (m/z 1251), loss of acyl mannose (m/z 1013), loss of C16:0 acyl (m/z 1157), loss of C19:0 fatty acyl (m/z 1115) and acyl phosphoinositol dimannoside (m/z 803). Thus, analysis of compounds of molecular weight under 2000 mu showed that LprG binds at least four structurally related molecules, each of which is composed of phosphatidylinositol as the core structure, but differ in the number of mannose units and fatty acyl chains.

In comparative nanoelectrspray analysis of eluents of NA-LprG, NA-NA-LprA, the three diacylated compounds were detected in association with all three proteins (FIG. 6B-D), suggesting that both LprG and LprA bind diacylated ligands. Association of all three diacylated compounds was decreased with NA-LprG-V91W, consistent with alteration of the hydrophobic putative binding pocket by this point mutation. While diacylated molecules were associated with both NA-LprG and NA-LprA, the triacylated molecule $Ac_1PIM2$ was associated preferentially with NA-LprG and was not associated with NA-LprA or NA-LprG-V91W (FIG. 6E). While these studies did not address triacylated glycolipids of higher molecular weight, these results demonstrate that LprG binds triacylated $Ac_1PIM2$ and suggest that LprG may also bind other Mtb glycolipids that include the $Ac_1PIM2$ structure (e.g. LM and LAM).

Figure 5C:
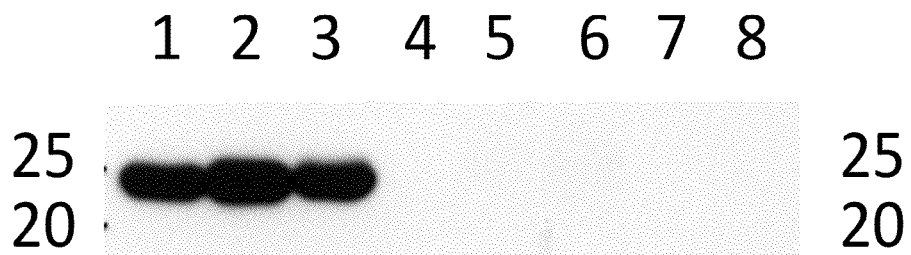
FIG. 5 illustrates immunoblots showing Mycobacterial glycolipids are associated with NA-LprG. SDS-PAGE analysis of proteins purified from M. smegmatis. Samples were visualized by silver stain (A, left panel), Pro-Q stain for carbohydrates (A, right panel), polyclonal anti-BCG Western blot (B) and anti-His$_6$ Western blot (C).

To directly test the ability of NA-LprG to bind specific candidate glycolipids and deliver them for recognition by TLR2, we purified NA-LprG from *E. coli* (with little or no TLR2 activity) and incubated it with preparations of mycobacterial glycolipids, including LM and LAM from *M. smegmatis*. After incubation with glycolipid, NA-LprG was repurified and tested for TLR2 agonist activity (FIG. 7). NA-LprG was able to bind and deliver them for recognition by TLR2. In contrast, NA-LprA did not bind and deliver these glycolipids, and NA-LprG-V91W bound them at reduced levels, consistent with prior evidence for their relatively specific association with NA-LprG (FIG. 5) suggesting that delivery by NA-LprG enhances the bioavailability or delivery of the TLR2 agonists, or enhances their recognition by TLR2. We conclude that NA-LprG is able to bind mycobacterial glycolipids and enhance their recognition by TLR2.

Figure 8:
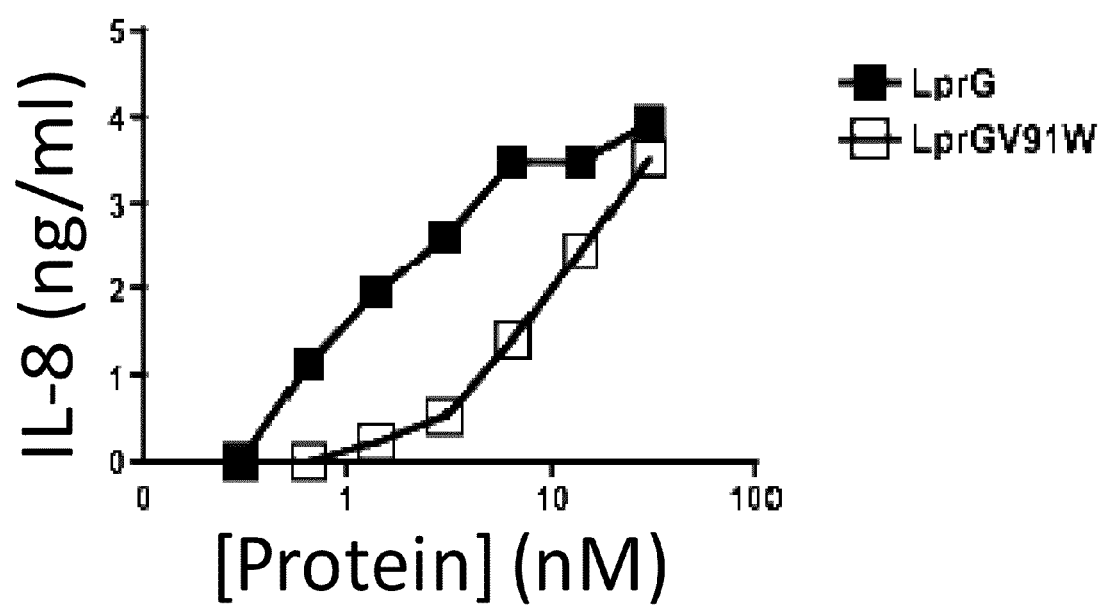
FIG. 8 illustrates plots showing the glycolipid binding site contributes significantly to the total TLR2 agonist activity of acylated LprG. HEK.293.TLR2-CD14 cells were used to assess TLR2 agonist activity of acylated LprG and LprG-V91W as in FIG. 1. Data are reported as the mean+/−SD of triplicate HEK293.TLR2-CD14 assays from a representative of at least 3 independent experiments.

Since the preceding studies were performed with non-acylated variants of the lipoproteins, one question is how significant the glycolipid binding site and chaperoned TLR2 agonist are in terms of the total TLR2 agonist activity of acylated LprG. Acylated LprG-V91W was found to be significantly less potent than wild-type acylated LprG (FIG. 8). These results suggest that alteration of the putative glycolipid binding site may reduce glycolipid binding or alter the types of glycolipids bound to favor those with less TLR2 agonist activity (consistent with results with NA-LprG), and reduced binding of glycolipid TLR2 agonists significantly reduces TLR2 agonist activity of LprG. Thus, mutation of the putative glycolipid binding site reduces TLR2 agonist activity of acylated LprG, indicating that TLR2 agonist activity of LprG reflects significant contributions by TLR2 agonists chaperoned by LprG as well as acylation of LprG itself.

Materials and Methods

Cloning and Expression of 6× Histidine ($His_6$) Tagged Proteins

LprA and NA-LprA were cloned previously. LprG was amplified from Mtb H37Rv genomic DNA by PCR using the 5' primer GCATATCCATATGCGGACCCCCAGACGCCACTG (SEQ ID NO: 3) and the 3' primer GTACAAGCTTGCTCACCGGGGGCTTCG (SEQ ID NO: 4). A non-acylated (NA) variant of LprG was cloned by using a 5' primer that excluded the signal sequence and changed the acylated cysteine to a methionine. NA-LprG was cloned with the following primers (underlined sequence is restriction enzyme recognition site): 5' gcaattccatatgtcgtcgggctc (SEQ ID NO: 5) and 3' gtacaagcttgctcaccgggggcttcg (SEQ ID NO: 6). Fusions of NA-LprA and NA-LprG were produced by digestion of the NA-Lpr constructs with NdeI, mscI, and HindIII, and ligating the 5' fragment of NA-LprA with the 3' fragment of NA-LprG to make the A:G fusion protein. For the G:A fusion, the same digest was performed, and 5' NA-LprG was fused with the 3' NA-LprA fragment. Site-directed mutagenesis of NA-LprG was performed using the Quikchange site directed mutagenesis kit (Stratagene, 200519) with the following primers: 5' gccgcgacgggaaactggaagctcacgctgggt (SEQ ID NO: 7) and 3' acccagcgtgagcttcagtttcccgtcgcggc (SEQ ID NO: 8). For expression in *M. smegmatis*, constructs were digested with NdeI and HindIII (NEB, Ipswitch, Mass.) and ligated into the shuttle vector pVV16 (provided by J. Belisle, Colorado State University, Fort Collins, Colo.) behind the constitutively active hsp60 promoter and in-frame with a c-terminal $His_6$ tag. For expression in *E. coli* Rosetta (EMD, cat#), constructs were digested with NdeI and HindIII and ligated with the expression plasmid pET-22b(+) (Novagen) removing the pelB leader sequence, behind the IPTG-inducible T7 promoter and in frame with a c-terminal $His_6$ tag. All constructs were verified by sequencing and analyzed using Clone Manager (SciEd software, Cary, N.C.). *M. smegmatis* was transformed by electroporation with a Gene Pulser (Bio-Rad, Hercules, Calif.) set at 2.5 kV, 25 µF, and 800 Ohms. $His_6$-tagged proteins were expressed in *M. smegmatis* $MC^2$ 1-2C(R. Wilkinson, Imperial College, London, U.K.) cultivated in Middlebrook 7H9 broth (Difco, Lawrence, Kans.) supplemented with 1% casamino acids (Fisher, Pittsburgh, Pa., BP1424), 0.2% glycerol (Fisher G33-1), 0.2% glucose, and 0.05% Tween 80. Kanamycin was used at 30 µg/ml for selection of *M. smegmatis*. For expression in *E. coli*, chemically competent *E. coli* Rosetta (EMD, cat#) were transformed according to the manufacturer's protocol. $His_6$-tagged proteins were expressed in *E. coli* Rosetta cultivated in Lurie-Bertani broth (LB), induction of gene expression was achieved by addition of 500 nM IPTG (Invitrogen, 15529-019) when culture $OD_{600}$ was approximately 1.0, with 2-3 h subsequent growth at 37° C. before collection of the cells by centrifugation. Co-selection with Ampicillin (50 ug/ml) and Chloramphenicol (34 ug/ml) were used for *E. coli* Rosetta expression strains. Bacteria were isolated by centrifugation at 6000×g for 20 min at 4° C.

Lysis and Purification of $His_6$-Tagged Proteins

Purification of NA-LprA and NA-LprG was accomplished as reported previously. Cells were resuspended in lysis buffer (2.5 ml/liter of bacterial culture) consisting of 50 mM NaH$_2$PO$_4$, 300 mM NaCl, 20 mM imidazole, pH 8.0, 2.5% protease inhibitor cocktail (Sigma P8849), 75 U/ml benzonase (Novagen, Madison, Wis., 70664-3), and 2.5 mg lysozyme (Sigma L-3790) and incubated for 15 min at 37° C. Bacteria were disrupted mechanically by 4 passages through a French press (2000 psi). Insoluble material was removed from the lysate by ultracentrifugation at 100,000×g for 1 h at 4° C., and supernatant was incubated directly with Ni-NTA beads (Qiagen, Valencia, Calif., 1018244) for 2-4 h at 4° C. Ni-NTA beads were transferred to polypropylene columns, washed 3× with 25 volumes of wash buffer (50 mM NaH$_2$PO$_4$, 1 M NaCl, 20 mM imidazole, 10% glycerol, pH 8.0), and bound protein was dissociated with elution buffer (50 mM NaH$_2$PO$_4$, 300 mM NaCl, 450 mM imidazole, pH 8.0). To prepare for anion exchange chromatography, sample was desalted into 20 mM Tris, pH 8.0 using PD-10 columns (GE Healthcare, Uppsala, Sweden 17-085-01). Samples were subjected to anion exchange chromatography using quaternary ammonium columns (GE Healthcare, 17-5053-01), and eluted with the addition of NaCl in the following steps: 50, 150, 200, 1000 mM. Presence and purity of desired protein was verified by SDS-PAGE and visualized as single bands by silver stain and anti-His$_6$ Western blot; yields were estimated by BCA protein assay (Pierce, Rockford, Ill., 23225). Material eluted by 50 and 150 mM NaCl was used for all experiments.

Culture of Mtb H37Ra

Mtb strain H37Ra (ATCC 25177) was cultured with shaking at 37° C. to late log phase growth (2.5 weeks) in Mtb 7H9 broth (4.7 g/17H9 (Difco 271310), 5 ml/l glycerol, 0.5 ml/l Tween-80 (Sigma, St. Louis, M0, P4780) supplemented with 10% albumin/dextrose/catalase (BD, Franklin Lakes, N.J. 212352). Bacilli were harvested by centrifugation at 5,000×g for 20 min at 4° C. 100 ml of late log phase culture was harvested by centrifugation and resuspended in 5 ml volume with culture supernatant and stored at −80° C.

Crystallization and Determination of NA-LprG Structure

Visualization of the crystal structure and design of mutation studies was performed using Deepview 4.0. Predicted structures of LprA and the fusions between LprA and LprG were generated using SWISS-MODEL. Molecular graphics images were produced using the UCSF Chimera package from the Resource for Biocomputing, Visualization, and Informatics at the University of California, San Francisco (NIH P41 RR-01081).

Charging of E. coli-Derived Proteins

For charging of E. coli-expressed proteins with M. smegmatis or Mtb H37Ra sonicate, thawed aliquots of cells suspended in 5 ml of medium were sonicated at amplitude 1 for four 15 minute bursts in ice water with a temperature cut-off of 40° C. Insoluble material was removed from the sonicate by centrifugation at 10,000×g for 20' at 4° C. The supernatant was incubated with 300-500 µg of protein for 3 h, rocking at 37° C. Charged proteins were re-purified by Ni-NTA affinity and anion-exchange chromatography. Proteins purified from E. coli were similarly charged with purified glycolipids or culture filtrate. In these experiments, 100 µg of E. coli-expressed, purified His$_6$-tagged protein was incubated with 50 µg of purified glycolipid or 100 µl of lysis buffer for 3 h at 37° C. The His$_6$-tagged proteins were then re-purified by Ni-NTA affinity and anion exchange chromatography and used in bioassays.

SDS-PAGE and Visualization of Purified Proteins and Glycolipids

Gels (13% acrylamide) were cast and run using a Tris-HCl buffer system. Proteins were visualized with Silver Stain Plus (BioRad), and carbohydrates (including glycolipids) were visualized with Pro-Q 3000 (Molecular Probes). For Western analysis was performed with transfer of material to a PVDF membrane, which was blocked with 5% Milk in PBS supplemented with 0.1% Tween-20 (PBST) for 1 h and incubated overnight at 4° C. with antibody (rabbit polyclonal anti-BCG, 1:30,000, DAKO; mouse monoclonal anti-His$_6$, 1:1000, Santa Cruz; or mouse monoclonal anti-LAM antibody CS-35, provided by Colorado State University under the NIH TBVTRM contract). Blots were then washed three times in PBST, incubated for 2 h at room temperature with secondary goat anti-rabbit or horse anti-mouse antibodies diluted 1:2000 in PBST, and washed three times in PBST. Reactive bands were visualized with chemiluminescence (GE Healthcare).

Mass spectrometry and Identification of Ligands of NA-LprG

Mammalian Cell Culture

Unless otherwise specified, incubations with eukaryotic cells were performed at 37° C. in 5% CO$_2$ atmosphere. Standard medium was DMEM (Hyclone, Logan, Utah, ASK30773) supplemented with 10% heat-inactivated FCS, 50 µM 2-ME, 2 mM L-glutamine, 1 mM sodium pyruvate, 10 mM HEPES, pH 7.4, and penicillin/streptomycin (Hyclone). Stimulation medium was standard medium with serum concentration reduced to 0.2% FBS. Female C57BL/6J mice (8-16 weeks old) were obtained from the Jackson Laboratory, housed under specific pathogen-free conditions and used to produce macrophages. TLR1$^{-/-}$, TLR2$^{-/-}$ and TLR6$^{-/-}$ mice were generously provided by Shizuo Akira (Research Institute for Microbial Disease, Osaka University, Osaka, Japan) and were back-crossed to C57BL/6J mice a minimum of eight times. CD14 knockout mice (B6.129S-Cd14$^{tm1Frm}$/J) were obtained from the Jackson Laboratory, maintained under specific pathogen-free conditions and used to produce macrophages. CD14 knockout mice were compared to C57BL/6J mice and F2 hybrids of C57BL/6J and 129sv. Bone marrow cells were cultured for 7-12 d in standard medium supplemented with 25% LADMAC cell-conditioned medium. HEK293 cells stably expressing TLR2-YFP (HEK293.TLR2) were produced previously. HEK293 cells (ATCC CRL-1573) were stably transfected with the empty vector to produce a control HEK293.pcDNA3 cell line. Transfected HEK293 cell lines were maintained in HEK medium (DMEM supplemented with 10% heat-inactivated FCS (HyClone)) supplemented with ciprofloxacin (10 µg/ml) and geneticin (500 µg/ml). HEK293.TLR2-CD14 line was also purchased from Invivogen (Invivogen, cat #293-htlr2cd14, San Diego, Calif. 92121). These cells were cultured in HEK medium supplemented with 100 ug/ml Normocin, 100 ug/ml Hygromycin B, and 10 ug/ml Blasticidin.

Cytokine ELISAs

HEK293 cells were incubated in 96-well plates (20,000 cells/well) for 5-8 h in 90 µl of appropriate HEK medium and then for an additional 16 h with or without TLR2 agonist. Supernatant IL-8 concentration was quantified by ELISA (R&D, Minneapolis, Minn., DY208). Bone marrow-derived macrophages were incubated overnight at 100,000 cells/well in standard medium and then for 12 h in stimulation medium with or without agonist. Supernatants were collected and stored at −80'C. TNF-alpha in the supernatant was quantified by ELISA (BD Biosciences #558874, R&D DY410). The following synthetic TLR agonists were also used: Ultrapure E. coli LPS (Invivogen, San Diego, Calif., tlrl-pelps), FSL-1 (Invivogen, tlrl-fsl) and Pam$_3$CSK$_4$ (Invivogen, tlrl-pms).

Having described the invention, the following is claimed:

1. An adjuvant combination that stimulates an immune activation and/or response comprising:

at least one of a TLR2 agonist or a TLR4 agonist and a purified non-acylated or acylated *Myobacterium tuberculosis* LprG lipoprotein.

2. An immune stimulating complex comprising:

at least one of a TLR2 agonist or a TLR4 agonist and purified non-acylated or acylated *Myobacterium tuberculosis* LprG lipoprotein, the LprG lipoprotein being present in an amount effective to chaperone the TLR2 agonist or the TLR4 agonist to an immune receptor.

* * * * *

SEQUENCE LISTING

<160> NUMBER OF SEQ ID NOS: 8

<210> SEQ ID NO 1
<211> LENGTH: 244
<212> TYPE: PRT
<213> ORGANISM: Mycobacterium smegmatis

<400> SEQUENCE: 1

Met Lys His Pro Pro Cys Ser Val Val Ala Ala Thr Ala Ile Leu
1               5                   10                  15

Ala Val Val Leu Ala Ile Gly Gly Cys Ser Thr Glu Gly Asp Ala Gly
            20                  25                  30

Lys Ala Ser Asp Thr Ala Ala Thr Ala Ser Asn Gly Asp Ala Ala Met
            35                  40                  45

Leu Leu Lys Gln Ala Thr Asp Ala Met Arg Lys Val Thr Gly Met His
        50                  55                  60

Val Arg Leu Ala Val Thr Gly Asp Val Pro Asn Leu Arg Val Thr Lys
65              70                  75                  80

Leu Glu Gly Asp Ile Ser Asn Thr Pro Gln Thr Val Ala Thr Gly Ser
                85                  90                  95

Ala Thr Leu Leu Val Gly Asn Lys Ser Glu Asp Ala Lys Phe Val Tyr
            100                 105                 110

Val Asp Gly His Leu Tyr Ser Asp Leu Gly Gln Pro Gly Thr Tyr Thr
            115                 120                 125

Asp Phe Gly Asn Gly Thr Ser Ile Tyr Asn Val Ser Val Leu Leu Asp
        130                 135                 140

Pro Asn Lys Gly Leu Ala Asn Leu Leu Ala Asn Leu Lys Asp Ala Ser
145             150                 155                 160

Val Ala Gly Ser Gln Gln Ala Asp Gly Val Ala Thr Thr Lys Ile Thr
                165                 170                 175

Gly Asn Ser Ser Ala Asp Asp Ile Ala Thr Leu Ala Gly Ser Arg Leu
            180                 185                 190

Thr Ser Glu Asp Val Lys Thr Val Pro Thr Thr Val Trp Ile Ala Ser
            195                 200                 205

Asp Gly Ser Ser His Leu Val Gln Ile Gln Ile Ala Pro Thr Lys Asp
        210                 215                 220

Thr Ser Val Thr Leu Thr Met Ser Asp Trp Gly Lys Gln Val Thr Ala
225             230                 235                 240

Thr Lys Pro Val

<210> SEQ ID NO 2
<211> LENGTH: 238
<212> TYPE: PRT
<213> ORGANISM: Mycobacterium smegmatis

<400> SEQUENCE: 2

Met Leu Gly Met Gln Thr Arg Arg Arg Leu Ser Ala Val Phe Ala Ser
1               5                   10                  15

Leu Thr Leu Ala Thr Ala Leu Ile Ala Gly Cys Ser Ser Gly Ser Lys
            20                  25                  30

Gln Ser Gly Ala Pro Leu Pro Asp Pro Thr Ser Leu Val Lys Gln Ser
            35                  40                  45

Ala Asp Ala Thr Lys Asn Val Lys Ser Val His Leu Val Leu Ser Ile
        50                  55                  60

Gln Gly Lys Ile Ser Gly Leu Pro Ile Lys Thr Leu Thr Gly Asp Leu

-continued

```
                65                  70                  75                  80
Thr Thr Thr Pro Ala Thr Ala Ala Lys Gly Asn Ala Thr Ile Thr Leu
                    85                  90                  95
Gly Gly Ser Asp Ile Asp Ala Asn Phe Val Val Asp Gly Thr Leu
            100                 105                 110
Tyr Ala Thr Leu Thr Pro Asn Lys Trp Ser Asp Phe Gly Lys Ala Ser
        115                 120                 125
Asp Ile Tyr Asp Val Ser Val Leu Leu Asn Pro Asp Asn Gly Leu Gly
    130                 135                 140
Asn Ala Leu Ala Asn Phe Ser Asn Ala Lys Ala Glu Gly Arg Glu Thr
145                 150                 155                 160
Ile Asn Gly Gln Ser Thr Ile Arg Ile Ser Gly Asn Val Ser Ala Asp
                165                 170                 175
Ala Val Asn Lys Ile Met Pro Gln Phe Asn Ala Thr Gln Pro Val Pro
            180                 185                 190
Ser Thr Val Trp Val Gln Glu Thr Gly Asp His Gln Leu Val Gln Ala
        195                 200                 205
Asn Leu Gln Lys Ser Ser Gly Asn Ser Val Gln Val Thr Leu Ser Asn
    210                 215                 220
Trp Gly Glu Gln Val Gln Val Thr Lys Pro Pro Val Ser Ser
225                 230                 235
```

<210> SEQ ID NO 3
<211> LENGTH: 33
<212> TYPE: DNA
<213> ORGANISM: Mycobacterium smegmatis

<400> SEQUENCE: 3
gcatatccat atgcggaccc ccagacgcca ctg       33

<210> SEQ ID NO 4
<211> LENGTH: 27
<212> TYPE: DNA
<213> ORGANISM: Mycobacterium smegmatis

<400> SEQUENCE: 4
gtacaagctt gctcaccggg ggcttcg       27

<210> SEQ ID NO 5
<211> LENGTH: 24
<212> TYPE: DNA
<213> ORGANISM: Mycobacterium smegmatis

<400> SEQUENCE: 5
gcaattccat atgtcgtcgg gctc       24

<210> SEQ ID NO 6
<211> LENGTH: 27
<212> TYPE: DNA
<213> ORGANISM: Mycobacterium smegmatis

<400> SEQUENCE: 6
gtacaagctt gctcaccggg ggcttcg       27

<210> SEQ ID NO 7
<211> LENGTH: 33
<212> TYPE: DNA
<213> ORGANISM: Mycobacterium smegmatis

<400> SEQUENCE: 7

-continued

```
gccgcgacgg gaaactggaa gctcacgctg ggt                          33

<210> SEQ ID NO 8
<211> LENGTH: 33
<212> TYPE: DNA
<213> ORGANISM: Mycobacterium smegmatis

<400> SEQUENCE: 8
acccagcgtg agcttccagt ttcccgtcgc ggc                          33
```